United States Patent
Berghausen et al.

(10) Patent No.: US 9,067,896 B2
(45) Date of Patent: *Jun. 30, 2015

(54) CRYSTALLINE FORMS OF 3-(2,6-DICHLORO-3,5-DIMETHOXY-PHENYL)-1-{6-[4-(4-ETHYL-PIPERAZIN-1-YL)-PHENYLAMINO]-PYRIMIDIN-4-YL}-1-METHYL-UREA AND SALTS THEREOF

(75) Inventors: Joerg Berghausen, Lorrach (DE); Prasad K Kapa, Parsippany, NJ (US); Joseph McKenna, Nazareth, PA (US); Joel Slade, Flanders, NJ (US); Raeann Wu, Pine Brook, NJ (US); Zhengming Du, Parsippany, NJ (US); Frank Stowasswer, Murg (DE)

(73) Assignee: Novartis AG, Basel (CH)

( * ) Notice: Subject to any disclaimer, the term of this patent is extended or adjusted under 35 U.S.C. 154(b) by 80 days.

This patent is subject to a terminal disclaimer.

(21) Appl. No.: 13/514,308

(22) PCT Filed: Dec. 6, 2010

(86) PCT No.: PCT/US2010/059108
§ 371 (c)(1),
(2), (4) Date: Jun. 7, 2012

(87) PCT Pub. No.: WO2011/071821
PCT Pub. Date: Jun. 16, 2011

(65) Prior Publication Data
US 2012/0245182 A1    Sep. 27, 2012

Related U.S. Application Data

(60) Provisional application No. 61/267,155, filed on Dec. 7, 2009.

(51) Int. Cl.
| | |
|---|---|
| A61K 31/5377 | (2006.01) |
| A61K 31/506 | (2006.01) |
| A61K 31/505 | (2006.01) |
| C07D 413/12 | (2006.01) |
| C07D 403/12 | (2006.01) |
| C07D 239/28 | (2006.01) |
| C07D 239/48 | (2006.01) |

(52) U.S. Cl.
CPC .................................. C07D 239/48 (2013.01)

(58) Field of Classification Search
CPC ............ A61K 31/5377; A61K 31/506; A61K 31/505; C07D 413/12; C07D 403/12; C07D 239/28

USPC .......... 514/252.14, 235.8, 275; 544/122, 357, 544/322
See application file for complete search history.

(56) References Cited

U.S. PATENT DOCUMENTS 8,293,743 B2 *    10/2012    Kahn .......................... 514/249
2008/0312248 A1 *  12/2008    Bold et al. ............... 514/252.14

FOREIGN PATENT DOCUMENTS

| WO | WO2006/000420 A1 | 1/2006 |
| WO | WO 2006/000420 A1 | 1/2006 |
| WO | WO 2007/071752 A2 | 6/2007 |
| WO | WO2007/071752 A2 | 6/2007 |

OTHER PUBLICATIONS

D. J. W. Grant and J. K. Guillory, "Polymorphism in pharmaceutical solids" edited by H. G. Brittain, Marcel Dekker, D. J. W. Grant (chapter 1) p. 1-10; and J. K. Guillory (chapter 5) p. 183-226, 1999.
Mino R. Caria, "Crystalline Polymorphism of Organic Compounds", Topic in Current Chemistry, vol. 198, p. 163-208, (1998).
Byrn S. et al., "Pharmaceutical Solids: A Strategic Approach to Regulatory Considerations", Pharmaceutical Research, vol. 12, No. 7, p. 945-954, (1995).
Haynes D. A. et al., "Occurrence of Pharmaceutically Acceptable Anions and Cations in the Cambridge Database", Journal of Pharmaceutical Sciences, vol. 94, No. 10, p. 2111-2120, (2005).
Bavin, Mike et al., "Process Development—Polymorphism in Process Development", Chemistry & Industry No. 16, pp. 527-529, Aug. 21, 1989.
Mitsuru Hashida, "Formulation Design and Evaluation of Oral Dosage Form", Yakugyo Jiho Co.Ltd., pp. 76-79 and 171-172, Feb. 10, 1995 [English Translation].
Sashin Souyaku, "The Practice of Medical Chemistry", Last Volume (Japanese Edition), pp. 347-365, Sep. 25, 1999 [English Translation].
Teruzo Asahara et al., "Solvent Handbook", Kodansha Ltd., pp. 47-51, Sep. 1, 1985 [English Translation].
Gennaro, Alfonso R., Remington, The Science and Practice of Pharmacy, 17th Ed., pp. 1912-1920, 1985.

* cited by examiner

*Primary Examiner* — James O Wilson
*Assistant Examiner* — Ebenezer O Sackey
(74) *Attorney, Agent, or Firm* — Michelle Han; Gregory Houghton

(57) ABSTRACT

The present technology provides novel anhydrous and hydrated crystalline forms of 3-(2,6-dichloro-3,5-dimethoxy-phenyl)-1-{6-[4-(4-ethyl-piperazin-1-yl)-phenylamino]-pyrimidin-4-yl}-1-methyl-urea, amorphous and anhydrous crystalline polymorphs of its monophosphoric acid salt, and the hydrochloride salt, including its dihydrate. The present technology further provides methods for preparing the various forms, compositions containing them, and methods of treatment employing them.

15 Claims, 11 Drawing Sheets

CRYSTALLINE FORMS OF 3-(2,6-DICHLORO-3,5-DIMETHOXY-PHENYL)-1-{6-[4-(4-ETHYL-PIPERAZIN-1-YL) -PHENYLAMINO]-PYRIMIDIN-4-YL}-1-METHYL-UREA AND SALTS THEREOF

This application is a 371 of PCT/US2010/059108 filed Dec. 6, 2010, which claims benefit of U.S. Provisional Application No. 61/267,155 filed Dec. 7, 2009, which in their entirety are herein incorporated by reference.

FIELD OF INVENTION

The present technology relates to anhydrous polymorphs, hydrated polymorphs and amorphous forms of 3-(2,6-dichloro-3,5-dimethoxy-phenyl)-1-{6-[4-(4-ethyl-piperazin-1-yl)-phenylamino]-pyrimidin-4-yl}-1-methyl-urea, its salts, methods for preparing them, compositions containing them, and methods of treatment employing them.

BACKGROUND 3-(2,6-Dichloro-3,5-dimethoxy-phenyl)-1-{6-[4-(4-ethyl-piperazin-1-yl)-phenylamino]-pyrimidin-4-yl}-1-methyl-urea (described in U.S. Ser. No. 11/570,983, filed Jun. 23, 2005, and incorporated by reference in its entirety herein) has the structure of Formula I:

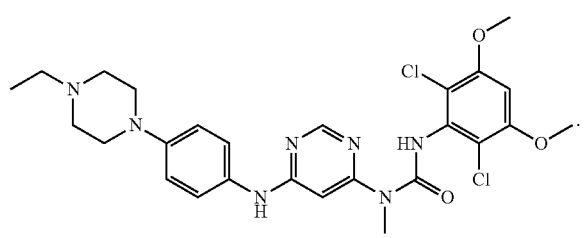

I

The compound of Formula I is a protein kinase inhibitor and is useful in the treatment of proliferative diseases mediated by protein kinases. In particular, the compound of Formula I inhibits FGFR1, FGFR2, FGFR3, FGFR4, KDR, HER1, HER2, Bcr-Abl, Tie2, and Ret kinases. It is therefore useful in the treatment of cancers including AML, melanocytic neoplasia, breast cancer, colon cancer, lung cancer (especially small-cell lung cancer), cancer of the prostate or Kaposi's sarcoma.

It is well known that the crystalline form of the active pharmaceutical ingredient (API) of a particular drug is often an important determinant of the drug's ease of preparation, hygroscopicity, stability, solubility, storage stability, ease of formulation, rate of dissolution in gastrointestinal fluids and in vivo bioavailability. Crystalline forms occur where the same composition of matter crystallizes in a different lattice arrangement resulting in different thermodynamic properties and stabilities specific to the particular crystalline form. Crystalline forms may also include different hydrates or solvates of the same compound. In deciding which form is preferable, the numerous properties of the forms are compared and the preferred form chosen based on the many physical property variables. It is entirely possible that one form can be preferable in some circumstances where certain aspects such as ease of preparation, stability, etc. are deemed to be critical. In other situations, a different form may be preferred for greater dissolution rate and/or superior bioavailability. It is not yet possible to predict whether a particular compound or salt of a compound will form polymorphs, whether any such polymorphs will be suitable for commercial use in a therapeutic composition, or which polymorphs will display such desirable properties.

SUMMARY

There are provided herein crystal and amorphous forms of the compound of Formula I, compositions including the crystal and amorphous forms, and methods of preparing the crystal and amorphous forms and compositions. The present technology further provides methods of using the crystal or amorphous forms of compounds of Formula I and compositions thereof to treat various diseases, including but not limited to, those that can be prevented, inhibited or ameliorated by inhibition of kinase activity selected from FGFR1, FGFR2, FGFR3, FGFR4, KDR, HER1, HER2, Bcr-Abl, Tie2, and Ret kinases.

DETAILED DESCRIPTION

In one aspect, the present technology provides anhydrous and hydrated crystalline forms of the compound of Formula I (the free base):

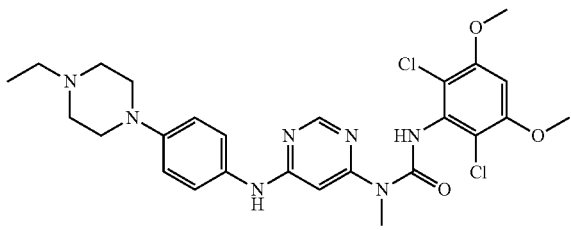

and phosphate salts thereof.

Figure 1A:
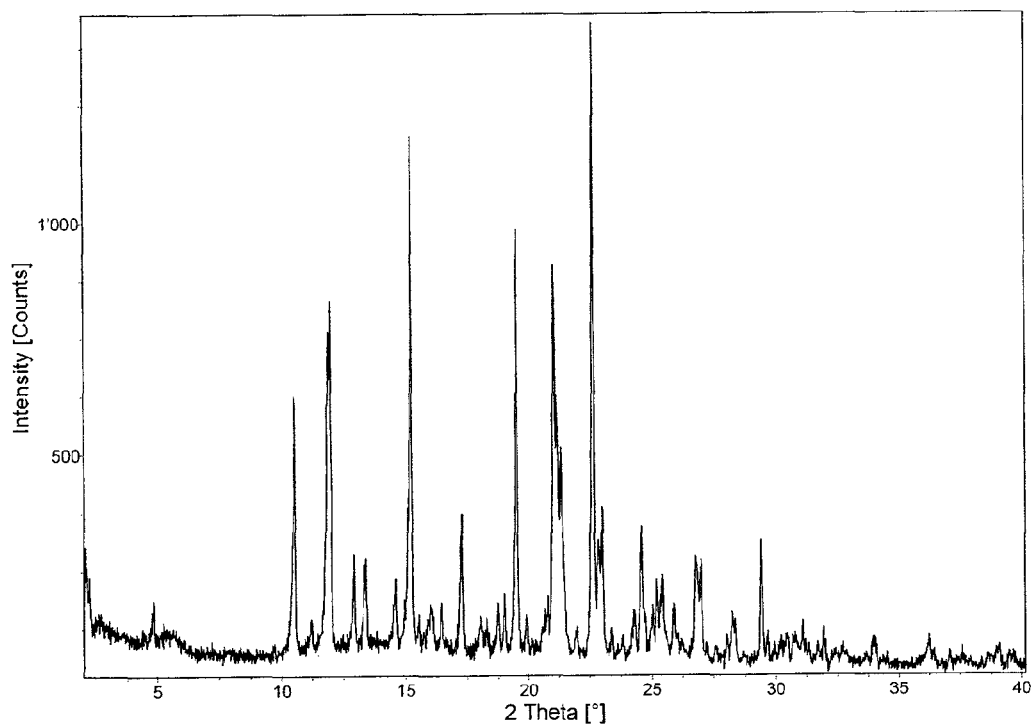
FIGS. 1A-E. XRPD of free base (FIG. 1A) of the compound of Formula I and its phosphate salts: form A (FIG. 1B); and form B (FIG. 1C), the free base monohydrate (FIG. 1D), and the hydrochloride dihydrate (FIG. 1E).

In one embodiment, the present technology provides an anhydrous crystalline form of the free base having an X-ray powder diffraction pattern comprising a characteristic peak, in terms of 2θ, at about 12°. In another embodiment, the X-ray powder diffraction pattern further comprises one or more characteristic peaks, in terms of 2θ, selected from peaks at about 10.5°, about 15.2°, about 19.5°, and about 21.0°. Thus, the X-ray powder diffraction pattern for an anhydrous form of the free base may comprise one, two, three, four, or five characteristic peaks, in terms of 2θ, selected from peaks at about 10.5°, about 12.0°, about 15.2°, about 19.5°, and about 21.0°. The X-ray powder diffraction pattern may further include one, two or three additional characteristic peaks, in terms of 2θ, selected from peaks at about 11.9°, about 21.3°, and about 22.6°. In another embodiment, the anhydrous crystalline form of the free base has an X-ray powder diffraction pattern substantially as shown in FIG. 1A. As used herein, the terms "about" and "substantially" indicate, with respect to values of 2θ, that such values for individual peaks can vary by ±0.4°. In some embodiments, the values of 2θ for individual peaks can vary by ±0.2°.

Figure 2A:
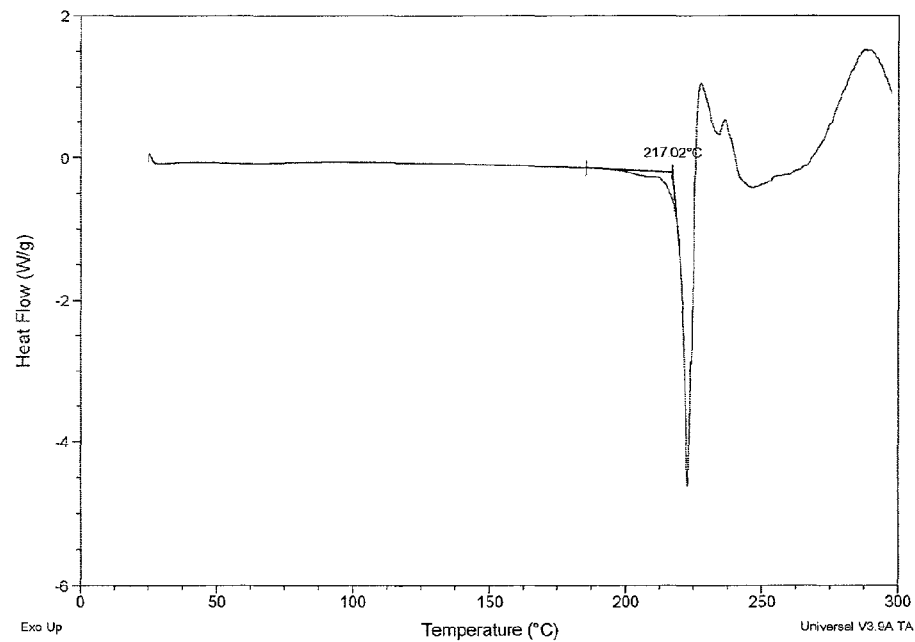
FIGS. 2A and 2B. DSC thermograms for the compound of Formula I as the anhydrous free base (FIG. 2A and as the phosphate salt (form A, FIG. 2B).

The anhydrous crystalline form of the free base may be characterized thermally. In one embodiment, the anhydrous crystalline form of the free base has a differential scanning calorimetry (DSC) thermogram showing an onset of an endotherm at about 217° C. In another embodiment, the anhydrous crystalline form of the free base has a differential scanning calorimetry thermogram substantially as shown in FIG. 2A. As used herein, the terms "about" and "substantially" indicate with respect to features such as endotherms, exotherms, baseline shifts, etc., that their values can vary ±2° C. For DSC, variation in the temperatures observed will depend upon the rate of temperature change as well as sample preparation technique and the particular instrument employed. Thus, the values reported herein relating to DSC thermograms can vary ±4° C.

Figure 8A:
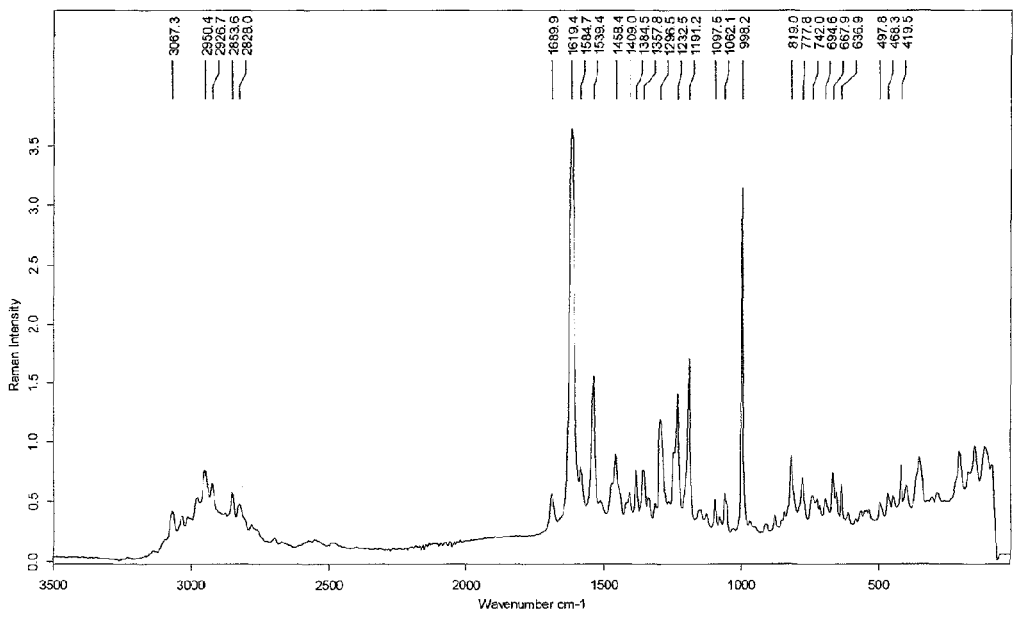
FIGS. 8A and 8B. Raman spectra of the compound of Formula I as the anhydrous free base (FIG. 8A) and as the monohydrate of the free base (FIG. 8B).

The anhydrous crystalline form of the free base may also be characterized by Raman spectroscopy. In one embodiment, the anhydrous crystalline form of the free base exhibits characteristic Raman peaks at about 2950, about 1619, about 1539, about 1297, about 1233, about 1191, and about 998 $cm^{-1}$. In some embodiments, the anhydrous crystalline form of the free base exhibits one or more further characteristic Raman peaks at about 3067, about 2927, about 2828, about 1690, about 1585, about 1458, about 1385, about 1358, about 1098, about 1062, about 819, about 778, about 695, about 668, about 637, about 498, about 468, and about 420 $cm^{-1}$. In another embodiment, the anhydrous crystalline form of the free base has a Raman spectrum substantially as shown in FIG. 8A. As used herein, the terms "about" and "substantially" indicate, with respect to wave number values, that such values for individual peaks can vary by ±2 $cm^{-1}$.

Figure 1B:
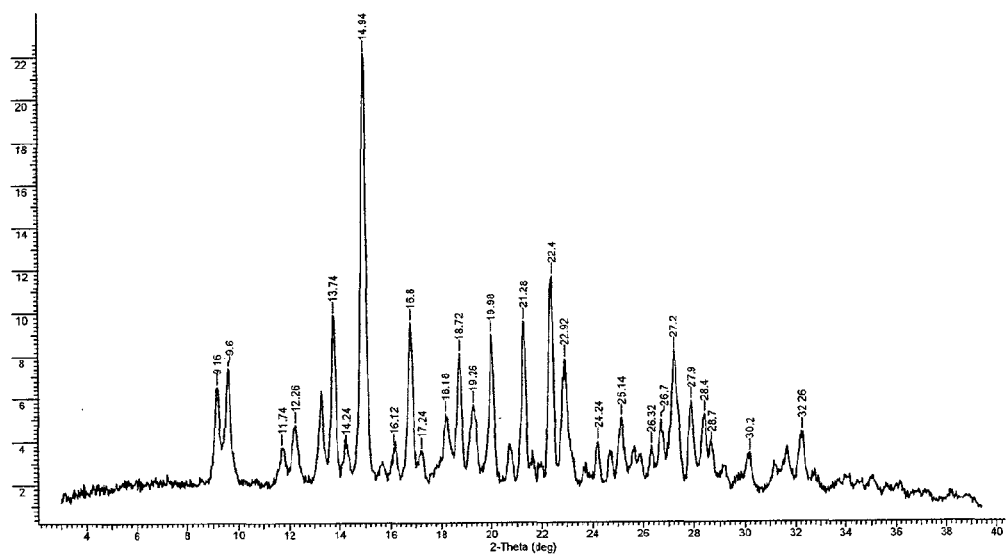
Figure 1C:
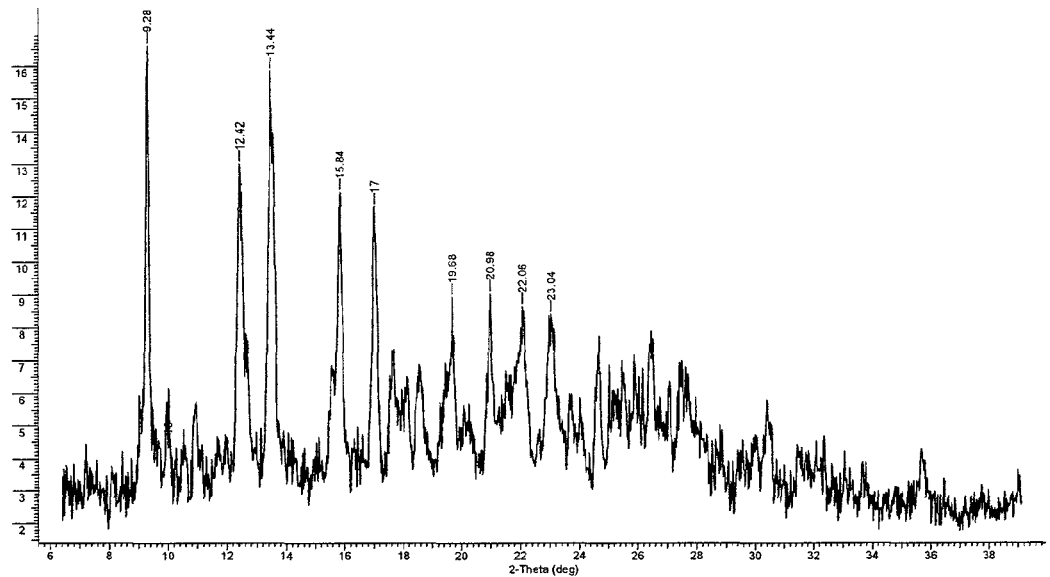
Figure 1D:
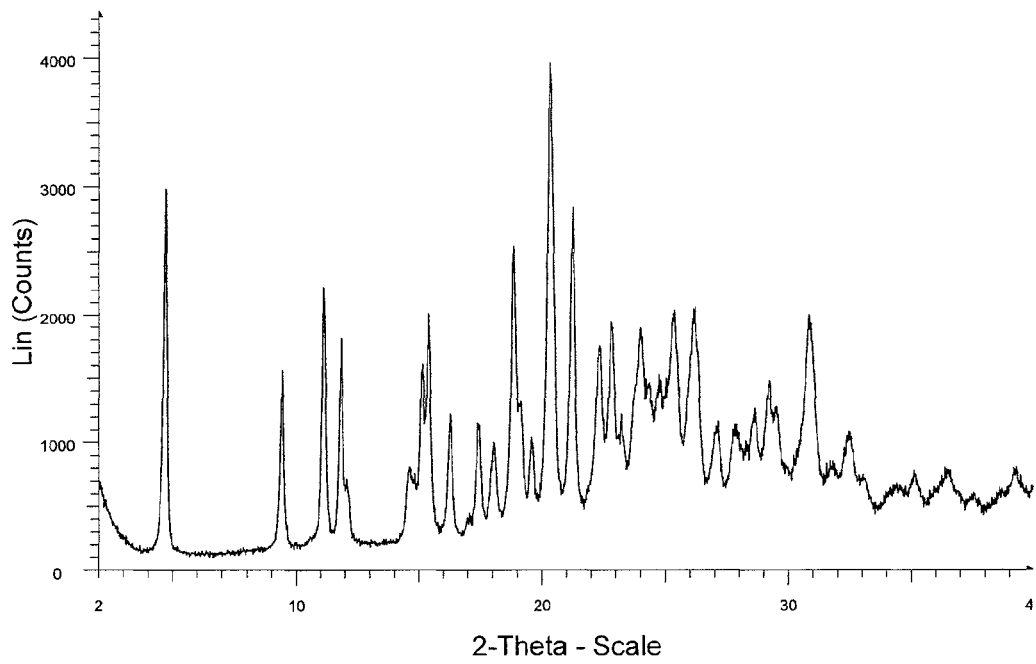

In one aspect, the present technology provides a crystalline monohydrate of the free base having an X-ray powder diffraction pattern comprising a characteristic peak, in terms of 2θ, at about 20.3°. In another embodiment, the X-ray powder diffraction pattern further comprises one or more characteristic peaks, in terms of 2θ, selected from peaks at about 21.2° and 19°. In another embodiment, the X-ray powder diffraction pattern further comprises one or more characteristic peaks, in terms of 2θ, selected from peaks at about 4.7°, about 9.4°, and about 11.0°. Thus, the X-ray powder diffraction pattern for a monohydrate form of the free base may comprise one, two, three, four, five, or six characteristic peaks, in terms of 2θ, selected from peaks at about 4.7°, about 9.4°, about 11.0°, about 18.8°, about 20.3°, and about 21.2°. The X-ray powder diffraction pattern for a monohydrate form of the free base may additionally include one, two, three, four, five, six or seven characteristic peaks, in terms of 2θ, selected from peaks at about 11.8°, about 15.3°, about 16.2°, about 19.1°, about 22.3°, about 22.8°, and about 25.3°. In another embodiment, the crystalline monohydrate form of the free base has an X-ray powder diffraction pattern substantially as shown in FIG. 1D.

Figure 7:
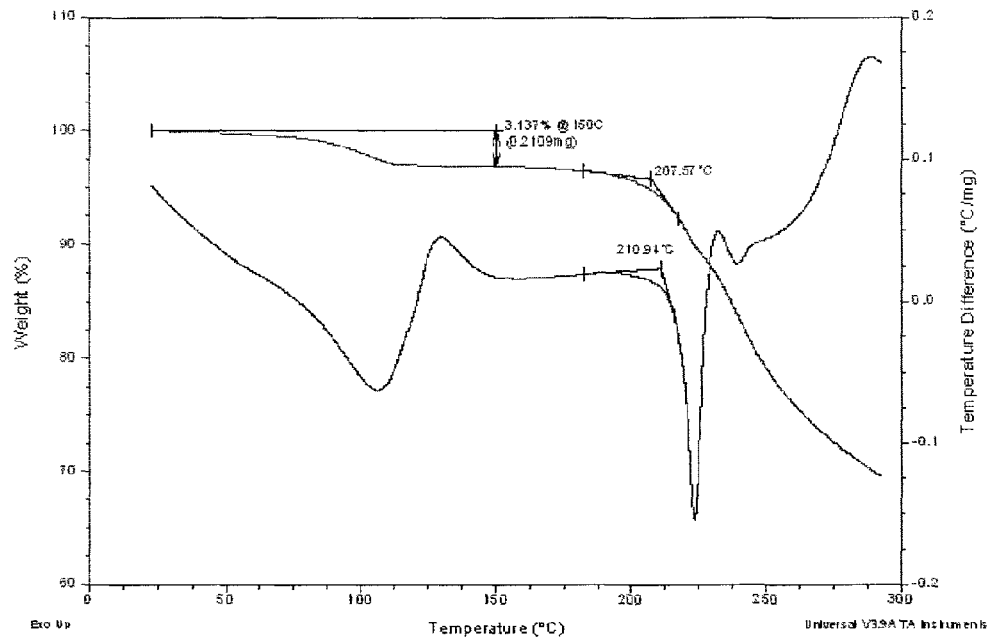
FIG. 7. DSC and TGA thermograms of the free base monohydrate.

The crystalline monohydrate form of the free base may be characterized thermally. In one embodiment, the crystalline monohydrate form of the free base has a DSC thermogram showing an onset of an endotherm at about 211° C. In another embodiment, the crystalline monohydrate form of the free base has a DSC thermogram and/or a TGA thermogram substantially as shown in FIG. 7. The TGA thermogram of FIG. 7 demonstrates that, based on the loss of about 0.2 mg from a sample mass of 6.7 mg, or 3.1% loss of weight, a water molecule (molecular weight 18) is lost from the monohydrate (molecular weight 578; and 18/578×100=3.1%).

Figure 8B:
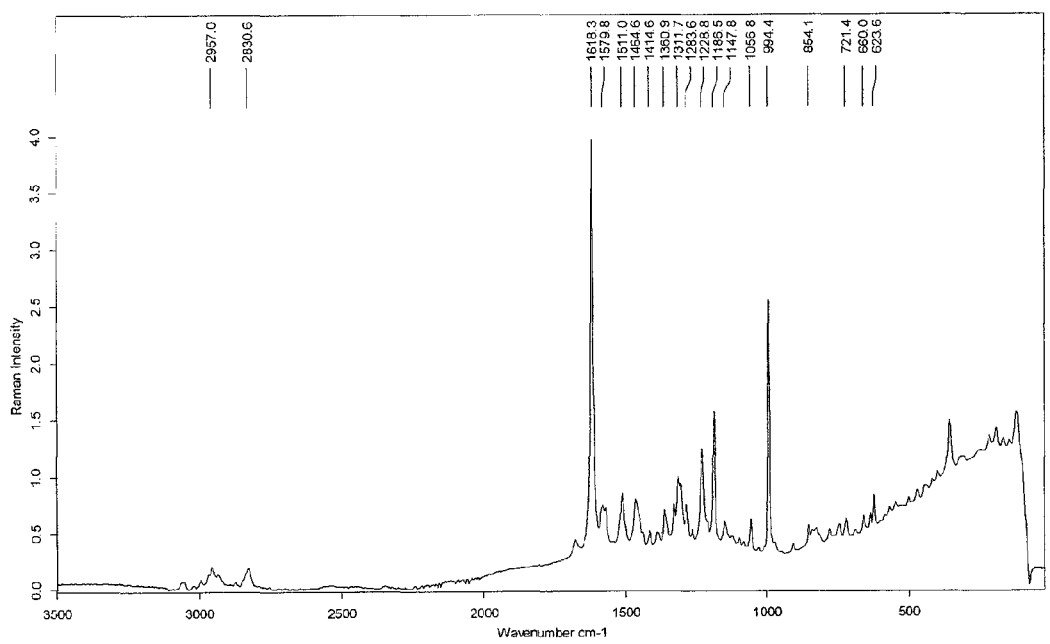

The monohydrate crystalline form of the free base may also be characterized by Raman spectroscopy. In one embodiment, the anhydrous crystalline form of the free base exhibits characteristic Raman peaks at about 2957, about 2831, about 1618, about 1511, about 1465, about 1361, about 1229, about 1186, and about 994 $cm^{-1}$. In some embodiments, the anhydrous crystalline form of the free base exhibits further characteristic Raman peaks at about 1580, about 1415, about 1312, about 1284, about 1184, about 1057, about 854, about 721, about 661, and about 624 $cm^{-1}$. In another embodiment, the monohydrate crystalline form of the free base has a Raman spectrum substantially as shown in FIG. 8B.

In another aspect, the present technology provides an anhydrous crystalline monophosphoric acid salt (or phosphate) of the compound of Formula I:

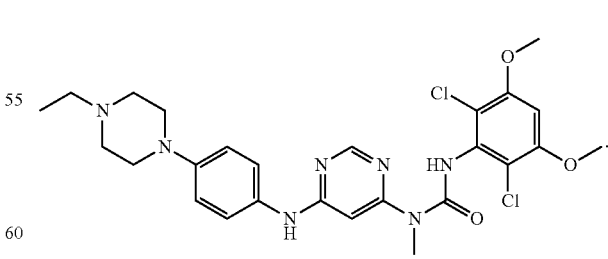

In another embodiment, the anhydrous crystalline monophosphoric acid salt is of form A which has an X-ray powder diffraction pattern comprising a characteristic peak, in terms of 2θ, at about 15°. In another embodiment, the X-ray powder diffraction pattern further comprises one or more characteristic peaks, in terms of 2θ, selected from peaks at about 13.7°, about 16.8°, about 21.3° and about 22.4°. In another embodiment, the X-ray powder diffraction pattern further comprises one or more characteristic peaks, in terms of 2θ, selected from peaks at about 9.2°, about 9.6°, about 18.7°, about 20.0°, about 22.9°, and about 27.2°. In another embodiment, the anhydrous crystalline form (form A) of a monophosphoric acid salt (or the phosphate salt) of the compound of Formula I has an X-ray powder diffraction pattern comprising at least three characteristic peaks, in terms of 2θ, selected from peaks at about 13.7°, about 15°, about 16.8°, about 21.3° and about 22.4°. Thus, the X-ray powder diffraction pattern for form A of the phosphate salt may comprise one, two, three, four, five, six, seven, eight, nine, ten or eleven characteristic peaks, in terms of 2θ, selected from peaks at about 9.2°, about 9.6°, about 13.7°, about 15°, about 16.8°, about 18.7°, about 20.0°, about 21.3° and about 22.4°, about 22.9°, and about 27.2°. In another embodiment, the anhydrous crystalline form (form A) of the phosphate salt has an X-ray powder diffraction pattern substantially as shown in FIG. 1B.

Figure 2B:
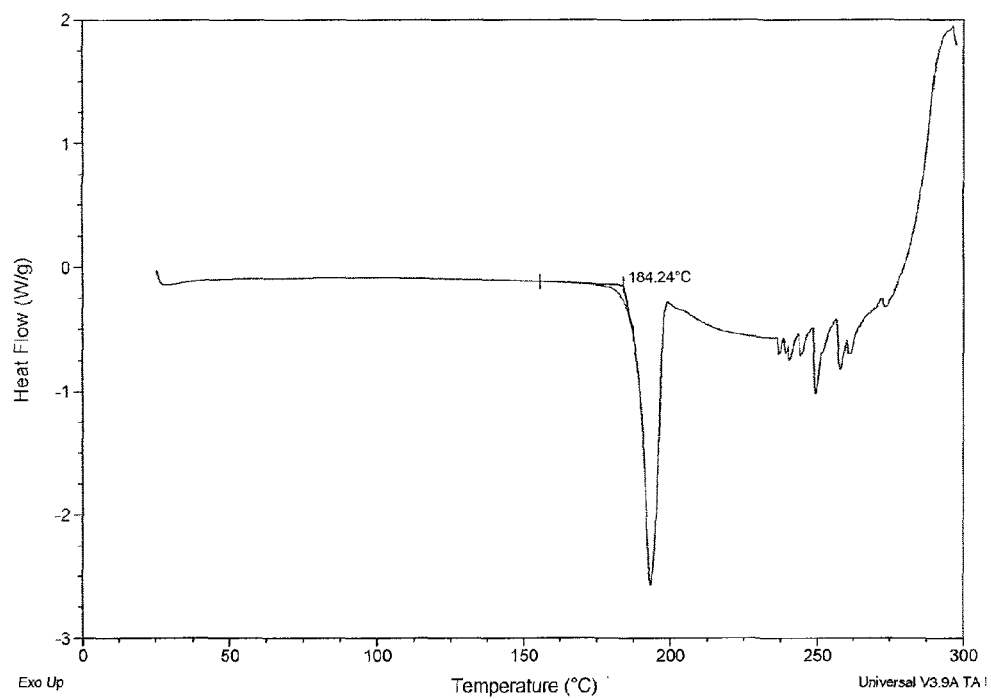

The anhydrous crystalline form of the phosphate salt (form A) may be characterized thermally. In one embodiment, the anhydrous crystalline form of the phosphate salt (form A) has a differential scanning calorimetry thermogram showing an onset of an endotherm at about 184° C. In another embodiment, the anhydrous crystalline form of the phosphate salt (form A) has a differential scanning calorimetry thermogram substantially as shown in FIG. 2B.

In another aspect, the present technology provides an anhydrous crystalline monophosphoric acid salt of form B which has an X-ray powder diffraction pattern comprising one or more characteristic peaks, in terms of 2θ, selected from peaks at about 9.3°, about 12.5°, about 13.4°, about 15.8°, and about 17°. In one embodiment, the form B of the phosphate salt has an X-ray powder diffraction pattern substantially as shown in FIG. 1C.

In one aspect, the present technology provides the amorphous form of the monophosphoric acid salt of the compound of Formula I:

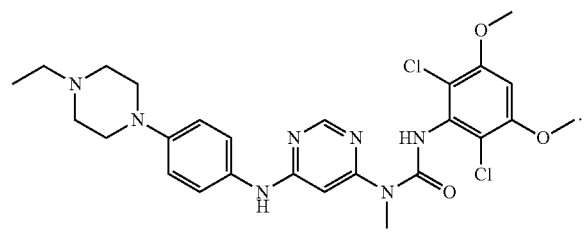

The XRPD of the amorphous form of the monophosphoric acid salt of the compound of Formula I does not display characteristic peaks. No apparent glass transition was observed by DSC for the amorphous form, but during TGA, the sample started to decompose at about 115° C., much lower than the form A of the crystalline phosphate salt.

In yet another aspect, the present technology provides the hydrochloric acid salt (or the hydrochloride) of the compound of Formula I:

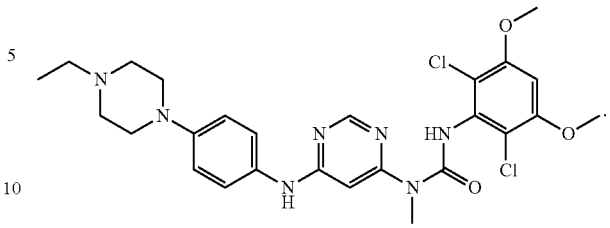

Figure 1E:
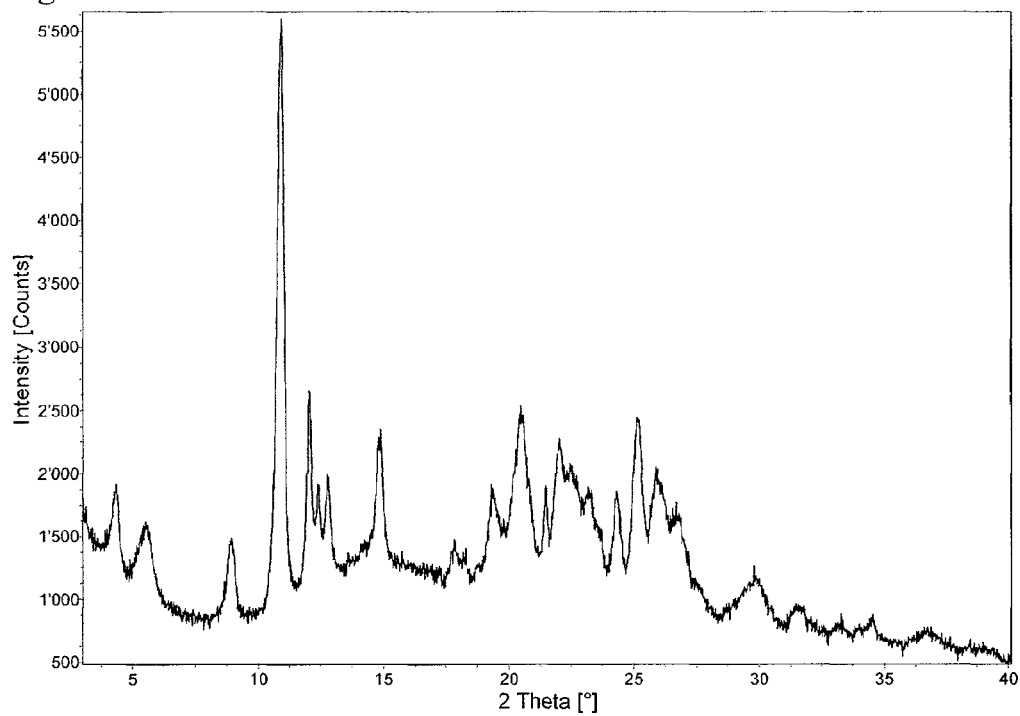

In one embodiment, the hydrochloride salt is the crystalline dihydrate. The dihydrate may have an X-ray powder diffraction pattern comprising one or more characteristic peaks, in terms of 2θ, selected from peaks at about 10.9°, about 12.1°, about 14.8°, about 20.5°, about 22°, and about 25.1°. In some embodiments, the hydrochloride salt has an X-ray powder diffraction pattern substantially as shown in FIG. 1E.

In addition to the techniques described above for characterizing crystalline forms of the present technology, XRPD, single crystal X-ray diffraction, DSC, dynamic vapor sorption (DVS), crystal morphology, solid state nuclear magnetic resonance, Raman scattering, infrared (IR) spectroscopy, may also be useful for characterization of other crystalline or amorphous forms of the present technology.

In another aspect, the present technology provides a method of making the anhydrous crystalline form of the phosphate salt of form A, comprising contacting a suspension of a compound of Formula I (the free base):

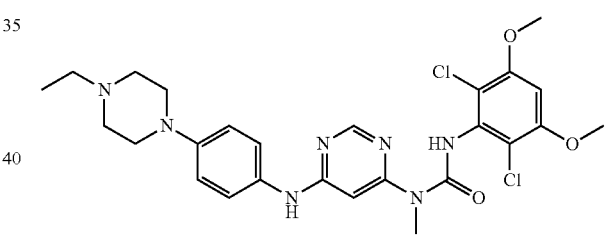

with phosphoric acid to provide the anhydrous crystalline form of the phosphate salt of form A. In one embodiment, the suspension of the compound of Formula I comprises isopropanol. In another embodiment, the method further comprises crystallizing the anhydrous crystalline form of the phosphate salt of form A from the suspension. In another embodiment, the method further comprises isolating the crystallized anhydrous crystalline form A.

In certain embodiments of the method, the phosphoric acid contacted is present in an amount from about 1 equivalent to about 10 equivalents, from about 2 equivalents to about 9 equivalents, from about 3 equivalents to about 8 equivalents, or from about 4 equivalents to about 7 equivalents, with respect to the molar amount of the free base contacted. In other embodiments, the phosphoric acid contacted is present in an amount from about 2 equivalents to about 4 equivalents or at about 3 equivalents with respect to the molar amount of the free base contacted. In certain embodiments, the suspension of the free base and the phosphoric acid are reacted or contacted from about 2 h to about 40 h, from about 4 h to about 20 h, or from about 8 h to about 10 h. In certain embodiments, the free base and the phosphoric acid are reacted at a temperature in the range of about 25° C. to about 100° C., about 40° C. to about 85° C., or about 55° C. to about 70° C. In certain embodiments, the free base and the phosphoric acid are reacted at a temperature at which a solvent employed in the reaction refluxes. In certain embodiments, the reaction is performed using reactants and one or more solvents that are substantially free of water (i.e., almost completely free of water).

The anhydrous crystalline form of the phosphate salt of form A obtained by the methods of the present technology may be further subjected to steps such as, e.g., drying, purification, etc. The isolated crystals may be subjected to drying at a suitable temperature. In one embodiment, the crystals are dried at a temperature in the range of about 20° C. to about 80° C. In some embodiments, the crystals are dried at a temperature in the range of about 30° C. to about 70° C. In some embodiments, the crystals are dried at a temperature in the range of about 40° C. to about 60° C. In one embodiment, the crystals are dried under reduced pressure in the range, for example, of about 10 mbar-about 40 mbar. The drying step may be conducted for a suitable period of time. Thus in one embodiment, the crystals are dried for a period of about 1 to about 72 hours, from about 2 to about 36 hours or from about 4 to about 18 hours. In some embodiments, the crystals are dried for about 48 h.

The phosphate salt of the compound of Formula I may be used to prepare the monohydrate of the free base. For example, the phosphate salt may be dissolved in an aqueous solution of an inorganic base, such as aqueous ammonium hydroxide. Over time, the free base precipitates out as a crystalline monohydrate. Optionally, additional steps such as filtration, washing and drying may be used to isolate the crystalline free base monohydrate, just as the phosphate salt was isolated as described above.

Crystalline forms of the present technology may be isolated in substantially pure form. By "substantially pure" it is meant that more than 50% by weight of 3-(2,6-dichloro-3,5-dimethoxy-phenyl)-1-{6-[4-(4-ethyl-piperazin-1-yl)-phenylamino]-pyrimidin-4-yl}-1-methyl-urea is present in one of the crystalline forms disclosed herein. In some embodiments of the isolated or substantially pure crystalline forms of the present technology, 3-(2,6-dichloro-3,5-dimethoxy-phenyl)-1-{6-[4-(4-ethyl-piperazin-1-yl)-phenylamino]-pyrimidin-4-yl}-1-methyl-urea is present at least about 60%, at least about 70%, at least about 80%, at least about 90%, at least about 95%, at least about 97%, at least about 98%, or at least about 99% by weight of the indicated form. For example, in certain embodiments, the present technology provides phosphate salts of the free base wherein at least about 50%, at least about 70%, at least about 80%, at least about 90%, at least about 95%, at least about 97%, at least about 98%, or at least about 99% by weight of the total phosphate salt of the free base is present as form A, form B or the amorphous form. In other embodiments, the present technology provides the free base such that at least about 50%, at least about 70%, at least about 80%, at least about 90%, at least about 95%, at least about 97%, at least about 98%, or at least about 99% by weight of the total of the free base is present as the crystalline anhydrous free base, the crystalline monohydrate of the free base, or the amorphous form of the free base. In still other embodiments, the present technology provides hydrochloride salts of the free base wherein at least about 50%, at least about 70%, at least about 80%, at least about 90%, at least about 95%, at least about 97%, at least about 98%, or at least about 99% by weight of the total is the amorphous or the crystalline dihydrate form of the hydrochloride salt.

The present technology also provides for pharmaceutical compositions and medicaments which may be prepared by mixing one or more anhydrous or hydrated crystalline or amorphous forms (of, e.g., the free base, the phosphate salts or the hydrochloride salts thereof) of the present technology, with pharmaceutically acceptable carriers, excipients, binders, diluents or the like to treat certain diseases as described herein.

Thus, in another aspect, the present technology provides compositions comprising an anhydrous or hydrated crystalline form or an amorphous form of the present technology and a pharmaceutically acceptable carrier, excipient, and/or diluent. In one embodiment, the anhydrous crystal form is of the compound of Formula I as the free base. In one embodiment, the hydrated crystal form is the monohydrate of the compound of Formula I as the free base. In another embodiment, the anhydrous crystalline form is of the monophosphoric acid salt of the compound of Formula I. In another embodiment, the anhydrous crystalline form of the monophosphoric acid salt is of form A. In another embodiment, the anhydrous crystalline form of the monophosphoric acid salt is of form B. In one embodiment, the monophosphoric acid salt of the compound of Formula I is amorphous. In another embodiment, the form is of the hydrochloride salt of the compound of Formula I. In an illustrative embodiment, the hydrochloride salt is the crystalline dihydrate or the amorphous form.

Such compositions can be in the form of, for example, granules, powders, tablets, capsules, syrup, suppositories, injections, emulsions, elixirs, suspensions or solutions. In one embodiment, the composition is substantially free of water. The instant compositions can be formulated for various routes of administration, for example, by oral and parenteral administration. Parenteral or systemic administration includes, but is not limited to, subcutaneous, intravenous, intraperitoneal, and intramuscular injections. The following dosage forms are given by way of example and should not be construed as limiting the instant technology.

Injectable dosage forms generally include oil suspensions or aqueous suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. In certain embodiments, such aqueous injectable forms are prepared (or reconstituted) immediately before administration to the subject. Alternatively, sterile oils may be employed as solvents or suspending agents. Typically, the oil or fatty acid is non-volatile, including natural or synthetic oils, fatty acids, mono-, di- or tri-glycerides.

For injection, the pharmaceutical compositions and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the pharmaceutical compositions may optionally contain stabilizers, pH modifiers, surfactants, bioavailability modifiers and combinations of these.

For oral, buccal, and sublingual administration, powders, suspensions, granules, tablets, pills, capsules, gelcaps, and caplets are acceptable as solid dosage forms. These can be prepared, for example, by mixing one or more anhydrous crystalline form of the present technology, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical compositions and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration. In certain embodiments, the liquid dosage forms, particularly of the crystalline forms of the free base monophosphate salt, are substantially free of water.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspensions of pharmaceutical compositions may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension pharmaceutical compositions.

Besides those representative dosage forms described above, pharmaceutically acceptable excipients and carriers are generally known to those skilled in the art and are thus included in the present technology. Such excipients and carriers are described, for example, in "Remingtons Pharmaceutical Sciences" Mack Pub. Co., New Jersey (1991), which is incorporated herein by reference.

The pharmaceutical compositions of the present technology may be designed to be short-acting, fast-releasing, long-acting, and sustained-releasing as described below. Thus, the pharmaceutical compositions may also be prepared for controlled release or for slow release.

The instant compositions may be administered in an extended release form to provide a prolonged storage and/or delivery effect. Therefore, the pharmaceutical compositions and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing therapeutically effective amounts are well within the bounds of routine experimentation and therefore, well within the scope of the present technology.

In certain other embodiments, the present technology provides compositions comprising the free base of the compound of Formula I, wherein at least about 50%, at least about 70%, at least about 80%, at least about 90%, at least about 95%, at least about 97%, at least about 98%, or at least about 99% by weight of the total free base in the composition is present as the anhydrous form, or as the monohydrate form. In further embodiments, the compositions of the present technology consist essentially of the free base, where at least about 95%, at least about 97%, at least about 98%, or at least about 99% of the free base is present in the composition as the anhydrous form, or as the monohydrate form.

In certain other embodiments, the present technology provides compositions comprising the phosphate salt of the free base wherein at least about 50%, at least about 70%, at least about 80%, at least about 90%, at least about 95%, at least about 97%, at least about 98%, or at least about 99% by weight of the total phosphate salt of the free base in the composition is present as form A, as form B, or as the amorphous form. In further embodiments, the compositions of the present technology consist essentially of a phosphate salt of the free base, where at least about 95%, at least about 97%, at least about 98%, or at least about 99% of the phosphate salt of the free base is present in the composition as form A, as form B, or as the amorphous form.

In some embodiments, the present technology provides compositions comprising the hydrochloride salt of the free base wherein at least about 50%, at least about 70%, at least about 80%, at least about 90%, at least about 95%, at least about 97%, at least about 98%, or at least about 99% by weight of the total hydrochloride salt of the free base in the composition is present as the dihydrate, or as the amorphous form. In further embodiments, the compositions of the present technology consist essentially of a hydrochloride salt of the free base, where at least about 95%, at least about 97%, at least about 98%, or at least about 99% of the phosphate salt of the free base is present in the composition as the dihydrate, or as the amorphous form.

In another aspect, the present technology provides a method of treatment comprising administering a therapeutically effective amount of an anhydrous or hydrated crystalline form or an amorphous form or a composition comprising an anhydrous or hydrated crystalline form or amorphous form of the present technology to a subject suffering from a disease, the pathology and/or symptoms of which disease can be prevented, inhibited or ameliorated by inhibition of a kinase activity wherein the kinase is selected from the group consisting of FGFR1, FGFR2, FGFR3, FGFR4, KDR, HER1, HER2, Bcr-Abl, Tie2, and Ret. In another embodiment, the present technology provides the use of the anhydrous or hydrated crystalline forms, the amorphous forms or the compositions including the anhydrous or hydrated crystalline forms or amorphous forms of the present technology in the manufacture of a medicament for treating a disease in a subject wherein the kinase activity of FGFR1, FGFR2, FGFR3, FGFR4, KDR, HER1, HER2, Bcr-Abl, Tie2, and Ret contributes to the pathology and/or symptoms of the disease. In some embodiments of the present technology, the kinase is selected from the group consisting of FGFR1, FGFR2, FGFR3, FGFR4.

Treatment within the context of the instant technology, means an alleviation, in whole or in part, of symptoms associated with a disorder or disease, or slowing or halting of further progression or worsening of those symptoms, or tending to prevent or ward off the disease or disorder in a subject at risk for developing the disease or disorder. Such disease or disorders include, but are not limited to carcinoma of the kidneys, liver, adrenal glands, bladder, breast, stomach, ovaries, colon, rectum, prostate, pancreas, lungs, vagina or thyroid; sarcoma; glioblastoma; leukemia; tumors of the neck or head; psoriasis; prostate hyperplasia; or neoplasia.

For example, within the context of treating diseases including a kinase mediated disorder as described above, a successful treatment may include an alleviation of symptoms or slowing or halting the progression of the disease, as measured by a reduction in levels or activity of one or more corresponding kinases. As used herein, a "therapeutically effective amount" refers to an amount of the anhydrous or hydrated crystalline form or amorphous form of the compound of Formula I (including the free base), or the anhydrous crystalline form or amorphous form of the phosphate salt of the compound of Formula I, they hydrochloride salt of the compound of Formula I (including the dihydrate or amorphous form) or compositions including them, that alleviates, in whole or in part, symptoms associated with the disorder or disease treated, or slows or halts of further progression or worsening of its symptoms, or prevents or provides prophylaxis for the disease or disorder in a subject at risk for developing the disease or disorder. A subject is any animal that can benefit from the administration of any of the forms of the compound of Formula I or a composition including it, as disclosed herein. In some embodiments, the subject is a mammal, for example, a human, a primate, a dog, a cat, a horse, a cow, a pig, a rodent, such as for example a rat or mouse. Typically, the mammal is a human.

A therapeutically effective amount of an anhydrous or hydrated crystalline form, or an amorphous form, or a composition comprising any such form of the present technology may vary depending upon the route of administration and dosage form. Effective amounts of the anhydrous or hydrated crystalline forms or amorphous forms of the compounds of Formula I typically fall in the range of about 0.01 up to 100 mg/kg/day, and more typically in the range of about 0.05 up to 25 mg/kg/day. Typically, the anhydrous or hydrated crystalline form, the amorphous form and the composition comprising such forms of the present technology, are selected to provide pharmaceutical compositions that exhibit high therapeutic indices. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology, thus generally described, will be understood more readily by reference to the following examples, which are provided by way of illustration and are not intended to be limiting of the present technology.

EXAMPLES

The following abbreviations are used throughout the present disclosure with respect to chemical and biological terminology:
DCM: Dichloromethane
DMSO: Dimethylsulfoxide
DSC: Differential scanning calorimetry
DVS: Dynamic vapor sorption
ESI-MS: Electrospray ionization-mass spectroscopy
FT-IR: Fourier transform-infrared
HPLC: High performance liquid chromatography
IPA: Isopropanol
M: Molar
MeOH: Methanol
N HCl: Normal HCl
NMR: Nuclear magnetic resonance spectroscopy
RH: Relative humidity
RT: Room temperature
SEM: Scanning electron microscopy
TGA: Thermo gravimetric analysis
UV: Ultraviolet
XRPD: X-ray powder diffraction General Methods, Instruments, and Standards Employed pH Value The pH of a solution was determined as exemplified: approximately 10 mg of the free base or its salt was transferred to a 20 ml vial and 10 ml of the corresponding buffer or water added to it. The solution was stirred continuously as the pH was measured. pH measurement can be carried out by a variety of methods, such as, by using micro pH electrodes.

Determination of Solubility

Excess free base (free base of Formula I), its phosphate salt (the monophosphoric acid salt of the free base), or another acid salt was equilibrated in solvents for 1 day at 25±0.5° C. The resultant slurry was filtered and the filtrate used for solubility determination by HPLC.

Intrinsic Dissolution

The intrinsic dissolution rate measurements were carried out in 0.5 $cm^2$ VanKel punch and die assemblies at a pellet pressure of 2000 pounds. The dissolution was measured using fiber optics dissolution system (C technologies Inc.) and a Cary UV/VIS spectrophotometer, with a stirring rate of 200 rpm. The solution medium was held at 37±0.5° C. and the concentration measurements were made at 260 nm.

Hygroscopicity

Hygroscopicity was measured from sorption/desorption isotherms using Surface Measurement System DVS-1 at 25±0.5° C. Samples were evaluated at various humidities including 75%, 85%, and 95%.

Polymorphism Behavior

Slurries of samples were stirred at high speed for 24 hours at 25±0.5° C., filtered, and the solid collected analyzed by XRPD.

HPLC Method

Instrument: Waters; Column: Symmetry C18, 3.5 micrometer particle diameter, 4.6×75 mm; column temperature: 35 degrees; flow rate: 1 mL/min; mobile phase: A=0.1% TFA in water and B=acetonitrile; detection: UV 254 nm; amount injected: about 2 micrograms; diluent: 60:40 (v/v) acetonitrile/0.2% aqueous phosphoric acid; and gradient: 10 to 70% B over 10 minutes.

TG Method

Instrument: TA instrument Q500; temperature range: room temperature to 300° C.; scan rate: 10° C./min; nitrogen flow: 60 ml/min. Mettler TGA 850; temperature range: room temperature to 300° C.; scan rate: 20° C./min; nitrogen flow: 40 ml/min.

SEM Method

Instrument: Jeol JSM 6300.

DSC method

Instrument: TA instrument Q1000; temperature range: room temperature to 210° C.; scan rate: 10° C./min; nitrogen flow: 60 mL/min.

X-Ray Crystallographic Method

Bruker AXS three-circle diffractometer with graphite-monochromated $Cu(K_\alpha)$-radiation from a fine focus sealed tube generator and a Smart 6000 CCD detector using the SMART software. Data processing and global cell refinement were performed with Saint. A semi-empirical absorption correction was applied, based on the intensities of symmetry-related reflections measured at different angular settings. The structures were solved by dual space-recycling methods and subsequent DF syntheses and refined based on full-matrix least-squares on $F^2$ using the SHELXTL program suite.

XRPD Method

Instrument: Bruker D8 Advance; irradiation: Cu Kα, (30 kV, 40 mA); variable slit V12 mm; scan range 2-40° (2 theta value); scan rate 0.3 s per step. Alternatively, XDS2000 by Scintag, Inc. was used; irradiation: Cu Kα (45 kV, 40 mA); divergence slice: 3 mm and 2 mm; measuring slice: 0.3 mm and 0.2 mm; chopper 0.02 grd; scan time: 6 minutes (3 minutes per frame); scan range: 2°-35° or 40° (2 theta value); scan rate 0.5°/min (2 theta value).

IR Method

Instrument: Thermo Magna 560; mode: transmission; scan range: $4000\ cm^{-1}$-$600\ cm^{-1}$.

Raman Method

Instrument: Bruker Vertex 70 FTIR; APT: 3.5 mm; 64 scans; RES 2.

Salt Screening

Example 1

Screening Acid Salts Of The Free Base Of Formula I

A salt screening experiment was performed with the free base of Formula I (prepared as described in Example 2 below) and a variety of different acids: acetic acid, benzoic acid, citric acid, fumaric acid, hippuric acid, hydrobromic acid, hydrochloric acid, lactic acid (D,L), maleic acid, malic acid (L), malonic acid, methanesulfonic acid, phosphoric acid, naphthalene-1,5-disulfonic acid, phosphoric acid, succinic acid, sulfuric acid, tartaric acid (D), and tartaric acid (L). The free base (30 mg) was dissolved in 12 mL THF. Aliquots of 0.1 ml of this solution were distributed to a 96 well format (Zinsser Crissy block) crystallization block. About 0.25 mg of the free base was delivered to each well; 0.044 ml of a 0.01M solution of the corresponding acids in acetone was also added to each well. The block was covered with a pre-slit lid and the solvent mixture was subsequently allowed to evaporate during about 10 hours at room temperature.

Attempts with acetic acid, benzoic acid, citric acid, hippuric acid, lactic acid, maleic acid, and malic acid yielded solids with the same XRPD pattern as that of the free base or of amorphous solids. Low crystallinity solids were obtained with fumaric acid, hydrobromic acid, naphthalene-1,5-disulfonic acid, sulfuric acid, or tartaric acids. For phosphoric acid, a crystalline salt form was obtained from 190 proof ethanol. Due to crystallinity or eventual synthetic ease, solids formed from phosphoric acid, hydrochloric acid, malonic acid, methanesulfonic acid, and succinic acid were evaluated further with respect to crystallinity and hygroscopicity.

The phosphate salt was found to be highly crystalline. Hygroscopicity as assessed by DVS sorption/desorption isotherms indicated that even at 95% RH, less than a 2% weight gain due to water absorption was observed. At 75% and 85% RH, less than a 1% weight gain was observed.

For the hydrochloride salt, several XRPD patterns were observed indicating the presence of more than one polymorph. Most of these salts had low crystallinity. The dihydrate was identified as the most crystalline. The hydrochloride salt was more hygroscopic than the phosphate salt. In one form of the hydrochloride salt, a weight gain of about 4.1% (75% RH) to about 16.9% (95% RH) was observed by DVS.

For the malonate salts, four forms were identified based on their observed XRPD patterns. The one evaluated further, demonstrated a fragile crystal, was only made once, had a wet pattern, and was hygroscopic (about 10% weight gain at all humidities tested).

For the methane sulfonic acid (or mesylate) salt, several XRPD patterns were observed of which only one could be made consistently but it was hygroscopic (exhibiting about 2.6% to 10% weight gain by DVS). Similarly, the succinate salt was also hygroscopic (exhibiting about a 4.1% to 10% weight gain by DVS).

Results of an initial solubility test in pH 3 buffer and in water are shown below in Table 1. The phosphate salt was more soluble than the methanesulfonate, malonate, and succinate salts in pH 3 buffer and in water. The phosphate salt was also more soluble in water than the free base.

TABLE 1

| Salt Type/Free Base | Medium/Solvent | Solubility (mg/ml) |
| --- | --- | --- |
| Methanesulfonate | pH3 Buffer | 0.003 |
| Malonate | pH3 Buffer | 0.003 |
| Succinate | pH3 Buffer | 0.002 |
| Phosphate | pH3 Buffer | 0.039 |
| Methanesulfonate | Water | 0.87 |
| Malonate | Water | 0.92 |
| Succinate | Water | 0.27 |
| Phosphate | Water | 1.7 |
| Free Base | pH3 Buffer | 0.20 |
| Free Base | Water | 0.001 |

Chemical Synthesis

Example 2

Manufacture of the Free Base of the Compound of Formula I

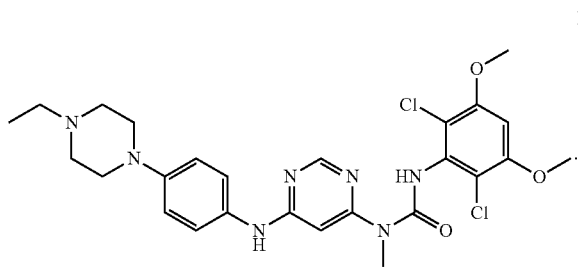

A. N-[4-(4-ethyl-piperazin-1-yl)-phenyl]-N'-methyl-pyrimidine-4,6-diamine

A mixture of 4-(4-ethylpiperazin-1-yl)-aniline (1 g, 4.88 mmol), (6-chloro-pyrimidin-4-yl)-methyl-amine (1.81 g, 12.68 mmol, 1.3 eq.), and 4N HCl in dioxane (15 ml) is heated in a sealed tube to 150° C. for 5 h. The reaction mixture is concentrated, diluted with DCM and a saturated aqueous solution of sodium bicarbonate. The aqueous layer is separated and extracted with DCM. The organic phase is washed with brine, dried (sodium sulfate), filtered and concentrated. Purification of the residue by silica gel column chromatography (DCM/MeOH, 93:7) followed by trituration in diethyl ether affords the title compound as a white solid: ESI-MS: 313.2 [MH]$^+$; $t_R$=1.10 min (gradient J); TLC: $R_f$=0.21 (DCM/MeOH, 93:7).

B. 4-(4-Ethylpiperazin-1-yl)-aniline

A suspension of 1-ethyl-4-(4-nitro-phenyl)-piperazine (6.2 g, 26.35 mmol) and Raney Nickel (2 g) in MeOH (120 mL) is stirred for 7 h at RT, under a hydrogen atmosphere. The reaction mixture is filtered through a pad of celite and concentrated to afford 5.3 g of the title compound as a violet solid: ESI-MS: 206.1 [MH]$^+$; TLC: $R_f$=0.15 (DCM/MeOH+ 1% NH$_3{}^{aq}$, 9:1).

C. 1-Ethyl-4-(4-nitro-phenyl)-piperazine

A mixture of 1-bromo-4-nitrobenzene (6 g, 29.7 mmol) and 1-ethylpiperazine (7.6 ml, 59.4 mmol, 2 eq.) is heated to 80° C. for 15 h. After cooling to RT, the reaction mixture is diluted with water and DCM/MeOH, 9:1. The aqueous layer is separated and extracted with DCM/MeOH, 9:1. The organic phase is washed with brine, dried (sodium sulfate), filtered and concentrated. Purification of the residue by silica gel column chromatography (DCM/MeOH+1% NH$_3{}^{aq}$, 9:1) affords 6.2 g of the title compound as a yellow solid: ESI-MS: 236.0 [MH]$^+$; $t_R$=2.35 min (purity: 100%, gradient J); TLC: $R_f$=0.50 (DCM/MeOH+1% NH$_3{}^{aq}$, 9:1).

D. (6-chloro-pyrimidin-4-yl)-methyl-amine

This material was prepared by a modified procedure published in the literature (*J. Appl. Chem.* 1955, 5, 358): To a suspension of commercially available 4,6-dichloropyrimidine (20 g, 131.6 mmol, 1.0 eq.) in isopropanol (60 ml) is added 33% methylamine in ethanol (40.1 ml, 328.9 mmol, 2.5 eq.) at such a rate that the internal temperature does not rise above 50° C. After completion of the addition the reaction mixture was stirred for 1 h at room temperature. Then, water (50 ml) is added and the suspension formed is chilled in an ice bath to 5° C. The precipitated product is filtered off, washed with cold isopropanol/water 2:1 (45 ml) and water. The collected material is vacuum dried over night at 45° C. to afford the title compound as colorless powder: $t_R$=3.57 min (purity: >99%, gradient A), ESI-MS: 144.3/146.2 [MH]$^+$.

E. (3-(2,6-Dichloro-3,5-dimethoxy-phenyl)-1-{6-[4-(4-ethyl-piperazin-1-yl)-phenylamino]-pyrimidin-4-yl}-1-methyl-urea)

The title compound was prepared by adding 2,6-dichloro-3,5-dimethoxyphenyl-isocyanate (1.25 eq.) to a solution of N-[4-(4-ethyl-piperazin-1-yl)-phenyl]-N'-methyl-pyrimidine-4,6-diamine (2.39 g, 7.7 mmol, 1 eq.) in toluene and stirring the reaction mixture for 1.5 h at reflux. Purification of the crude product by silica gel column chromatography (DCM/MeOH+1% NH$_3{}^{aq}$, 95:5) affords the title compound as a white solid: ESI-MS: 560.0/561.9 [MH]$^+$; $t_R$=3.54 min (purity: 100%, gradient J); TLC: $R_f$=0.28 (DCM/MeOH+1% NH$_3{}^{aq}$, 95:5). Analysis: $C_{26}H_{31}N_7O_3Cl_2$, calc. C, 55.72%; H, 5.57%; N, 17.49%; O, 8.56%; Cl, 12.65%. Found C, 55.96%; H, 5.84%; N, 17.17%; O, 8.46%; Cl, 12.57%. The title compound was characterized by XRPD, thermal and other methods as described below.

Example 3

Manufacture of the Monophosphoric Acid Salt Form A of the Compound of Formula I To a round bottom flask was added 3-(2,6-dichloro-3,5-dimethoxyphenyl)-1-{6-[4-(4-ethylpiperazin-1-yl)phenylamino]-pyrimidine-4-yl}-1-methyl-urea (134 g, 240 mmol) and IPA (2000 ml). The suspension was stirred and heated to 50° C. and a solution of phosphoric acid (73.5 g, 750 mmol) in water (2000 ml) added to it portions. The mixture was stirred at 60° C. for 30 min. and filtered through a polypropylene pad. The pad was washed with warm IPA/water (1:1, 200 ml) and the filtrates were combined. To this clear solution, IPA (6000 ml) was added and the mixture was stirred under reflux for 20 min, cooled slowly to room temperature (25° C.), and stirred for 24 hours. The white salt product was collected by filtration, washed with IPA (2×500 ml) and dried in the oven at 60° C. under reduced pressure for two days to provide the phosphate salt (form A) 110 g. Yield 70%. Purity>98% by HPLC. Analysis: $C_{26}H_{34}N_7O_7Cl_2P$, calc. C, 47.42%; H, 5.20%; N, 14.89%; O, 17.01%; Cl, 10.77%; P, 4.70%. Found C, 47.40%; H, 5.11%; N, 14.71%; O, 17.18%; Cl, 10.73%; P, 4.87%. The title compound was characterized by XRPD, thermal and other methods as described below.

Example 4

Manufacture of the Free Base Monohydrate Form of the Compound of Formula I

To a 22 l 4-neck round bottom flask at 18° C. under a nitrogen atmosphere was charged 15M ammonium hydroxide (10 L, 15 mole). To the solution was added the phosphate salt of 3-(2,6-dichloro-3,5-dimethoxyphenyl)-1-{6-[4-(4-ethylpiperazin-1-yl)phenylamino]-pyrimidine-4-yl}-1-methyl-urea (660 g, 1.002 mole; prepared by the method of Example 3) as a solid in portions at 18° C. over 1 hour. The resulting white suspension was stirred at 18° C. for 16 hours. A sample was removed and checked by $^1$H NMR to confirm the complete conversion of the phosphate salt to free base. The NMR showed complete conversion to free base. The mixture was filtered through a 3 L sintered glass funnel with a coarse frit (40-60 ASTM). The filtration was slow requiring ~3 hours due to the fine particle size of the solid free base. The solid was washed with deionized water (1 L). This wash was also very slow (required 1.5 hours). The solid was dried at 60° C. under vacuum (5 torr) for 16 hours to give 642 g of free base (114% of theory, theory=561.1 g). The dried solid was reslurried in deionized water (10.5 L) at 18° C. for 3 hours. The solid was filtered through a 3 L coarse frit sintered glass funnel with a coarse frit (40-60 ASTM). The filter cake was rinsed with deionized water (2 L). The solid was dried at 60° C. under vacuum (5 torr) for 16 hours to give the free base as a monohydrate (559 g, 96.7% of theory for a monohydrate).

Characterization of the Crystal Forms

Example 5

Figure 3A:
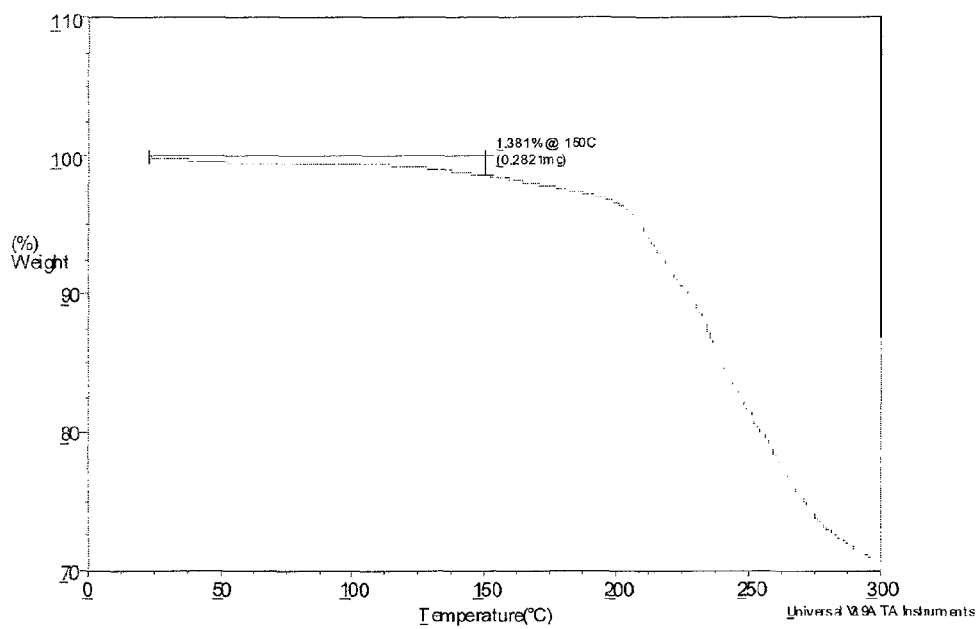
FIGS. 3A-3C. TGA thermograms for the compound of Formula I as the anhydrous free base (FIG. 3A), as the phosphate salt (form A, FIG. 3B), and as the hydrochloride salt (dihydrate, FIG. 3C).
Figure 5A:
FIGS. 5A and 5B. SEM micrographs of the compound of Formula I as the crystalline free base (FIG. 5A) and as the phosphate salt (form A, FIG. 5B).

Physicochemical Properties of the Free Base, the Phosphate Salt (Form A), and the Hydrochloride A. Free Base The anhydrous free base showed good crystallinity (for XRPD spectrum, see FIG. 1A). It was slightly hygroscopic, and upon heating at 10° C./min, melted at 217° C. (onset) with subsequent decomposition (for DSC thermogram, see FIG. 2A). The TGA for the anhydrous base is shown in FIG. 3A, and the observed weight loss is consistent with the anhydrous form. It was not soluble in aqueous media at high pH (ca. 0.00004 mg/mL in pH 6.8 buffer and ca 0.00009 mg/mL with pH 6.67 in water), and sparingly to slightly soluble in common organic solvents. In 0.1-N HCl, the anhydrous free base changes into another form (likely a form of hydrochloride). The monohydrate form of the free base also showed good crystallinity (for XRPD spectrum, see FIG. 1D). An SEM micrograph of the anhydrous free base is shown in FIG. 5A.

B. Phosphate Salt (Form A)

Figure 3B:
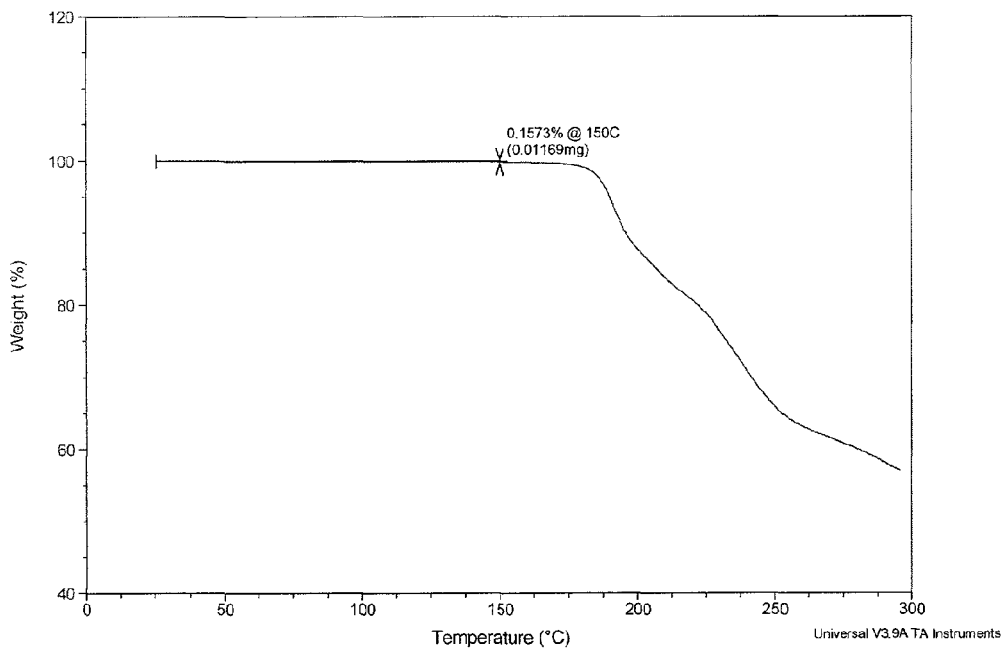
Figure 5B:
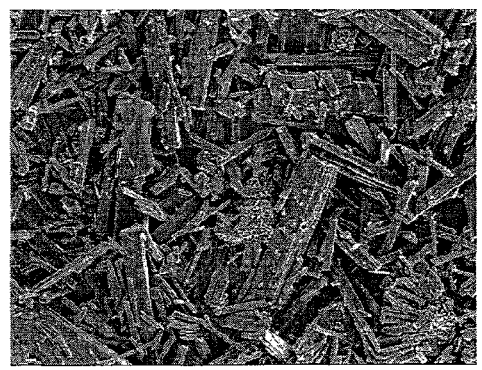
Figure 6:
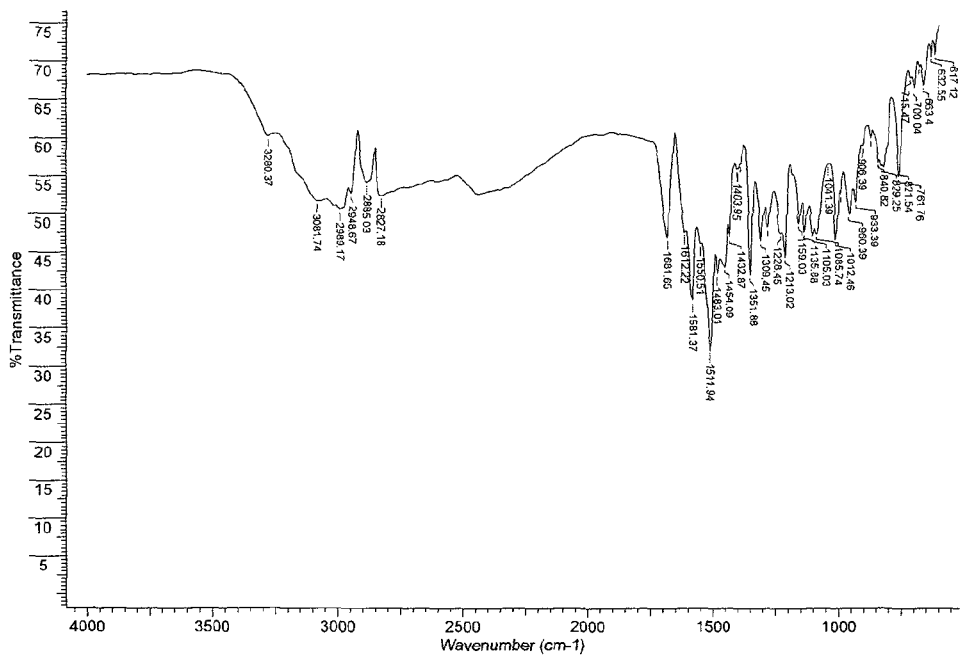
FIG. 6. FT-IR-spectrum of the phosphate salt (form A) of the compound of Formula I.

The phosphate salt showed good crystallinity (for XRPD spectrum, see FIG. 1B (phosphate salt (form A)). It was slightly hygroscopic, and upon heating at 10° C./min, melted at 184.0° C. (onset) with subsequent decomposition (See FIG. 2B (phosphate salt (form A)). The TGA of the phosphate salt is shown in FIG. 3B, and the observed weight loss is consistent with the anhydrous form. It was not soluble in pH 6.8 buffer (ca. 0.00009 mg/mL), but, unlike the free base, was soluble in water (1.3 mg/mL). It was sparingly soluble in common organic solvents. Additional solubility studies are presented below. The FT-IR spectrum of the phosphate salt (form A) is shown in FIG. 6. Up to 0.6% of residual solvent (isopropanol) was detected in the phosphate salt. An SEM micrograph of the phosphate salt, form A is shown in FIG. 5B.

C. Hydrochloride Salt of the Free Base

Figure 3C:
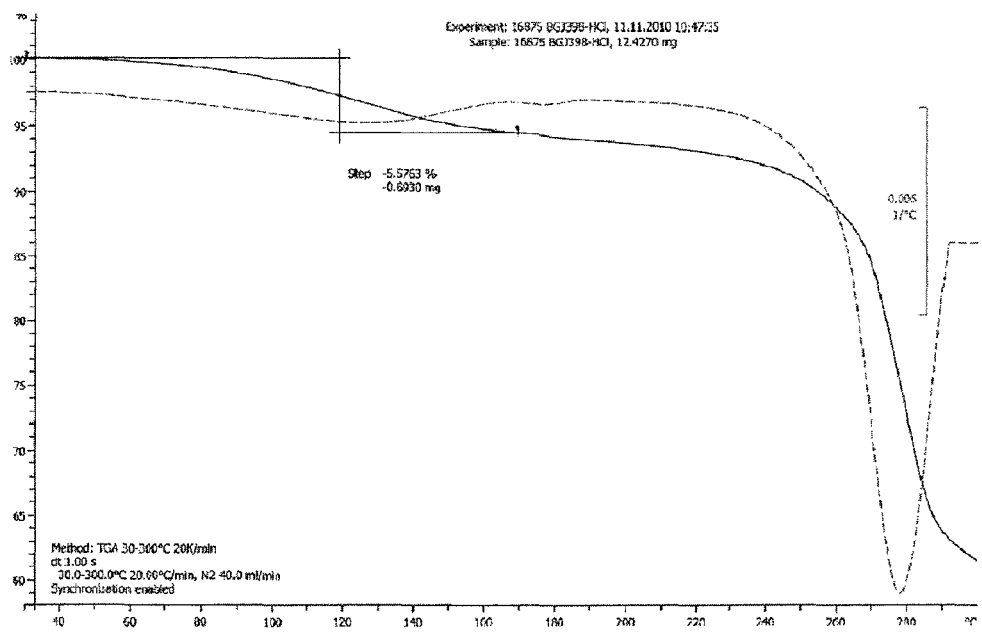

The hydrochloride salt showed moderate crystallinity (for XRPD spectrum, see FIG. 1E) in the dihydrate form. The TGA is shown in FIG. 3C, and the observed weight loss is consistent with the dihydrate form. The hydrochloride is hygroscopic and the present form is a dihydrate. Solubility studies are presented in Example 8, Table 3D.

Example 6

Amorphous Form of the Phosphate Salt of the Free Base

About 40 mg of phosphate salt (form A) was mixed with 4 ml of tetrahydrofuran/water (1:1) at 25° C. After stirring overnight, the solution was filtered. With no stirring, the clear filtrate was placed under nitrogen flow to dry. The solid, obtained after solvent evaporation, was further evaluated by DSC and TGA. No apparent glass transition was observed on DSC thermograph when subjected to heating from −40° C. to 140° C. On TGA thermograph, it was observed that the sample started to decompose at ~115° C., much lower than the form A of the crystalline phosphate salt. See also Example 15, below.

Example 7

Determining Intrinsic Dissolution Rates

The intrinsic dissolution rate was determined for the phosphate salt in water, pH=6.8 and 0.1N HCl, and for the free base monohydrate in pH=6.8, 4.5 and 0.1N HCl. The measurements were carried out on a VanKel instrument using a Cary UV/VIS spectrophotometer (Table 2). The phosphate salt demonstrated faster intrinsic dissolution rates in water and 0.1N HCl than the free base.

TABLE 2

Intrinsic Dissolution Rates

| Sample | Phosphate salt (form A) | Free base (monohydrate) |
|---|---|---|
| Sample mass | about 100 mg | about 100 mg |
| Wavelength for detection | 290 nm | 290.2 nm |
| Rotation of disc | 200 rpm | 50 rpm |
| Temperature | 37° C. | 37° C. |
| Measurement time | 20-60 Min | 400 Min |
| Dissolution medium | Intrinsic DR value mg/min/cm$^2$ | |
| HCl 0.1N | 1.0661 (Anhydrous Free Base: 0.28) | 0.3132 |
| pH = 6.8 | 0.0056 | 0.0026 |
| pH = 4.5 | n.d. | 0.0001 |
| Water | 0.3279 (Anhydrous Free Base: 0.01) | n.d. | n.d.—not determined

Example 8

Solubility in Aqueous Media and

Solubility of the monohydrate of the anhydrous and monohydrate free base was measured in various aqueous media (e.g., pH 6.8 buffer, pH 4.5 buffer, pH 1 buffer), including simulated and actual human fluids. The simulated fluid compositions are shown in table 3A-3C below.

TABLE 3A

SGF pH 2.0

| Excipient | Target amount/volume per 1 liter |
|---|---|
| NaCl | 2 g |
| Triton X-100 | 1 g |
| HCl 0.1M | 100 ml |
| Purified Water | q.s. |

TABLE 3B

FaSSIF pH 6.5

| Excipient | Molar Amount [mM] | Target amount [g/1 l] |
|---|---|---|
| Phosphoric Acid (85%) | 28.6 (as 100%) | 3.30 (as 85%) |
| Sodium taurocholate | 3 | 1.65 |
| Lecithin | 0.75 | 0.59 |
| NaCl | 105.8 | 6.186 |
| NaOH | | q.s. |
| Purified Water | | q.s. |

TABLE 3C

FeSSIF pH 6.5

| Excipient | Molar Amount [mM] | Target amount [g/1 l] |
|---|---|---|
| Acetic Acid glac. | 144 | 8.65 |
| Sodium taurocholate | 15 | 8.25 |
| Lecithin | 3.75 | 2.954 |
| NaCl | 202 | 11.87 |
| NaOH | | q.s. |
| Purified Water | | q.s. |

The human fluids were collected from 12 human subjects. The solubility was assessed as described above after 24 hours. Results are tabulated below in Tables 4A and 4B.

TABLE 4A

Solubility of Anhydrous Free Base

| Medium | Solubility in mg/ml after 24 h |
|---|---|
| Simulated Gastric Fluid (SGF) | 0.0497 |
| Fasted State Simulated Intestinal Fluid (FaSSIF) | 0.001 |
| Fed State Simulated Intestinal Fluid (FeSSIF) | 0.148 |
| pH 1 HCl | 0.052 |
| ph 4.5 Acetate | 0.008 |
| ph 6.8 Phosphate | <LOQ* |
| Human gastric fluid (HGF) | 0.001 |
| Human intestinal fluid, (HIF) fasted | 0.002 |
| HIF, fed | 0.004 |

*<LOQ: below limit of quantitation.

TABLE 4B

Solubility of Monohydrate Free Base

| Medium | Solubility in mg/ml after 24 h |
|---|---|
| SGF | 0.020 |
| FaSSIF | 0.003 |
| FeSSIF | 0.459 |
| pH 1 HCl | 0.103 |
| ph 4.5 Acetate | 0.054 |
| ph 6.8 Phosphate | <LOQ* |
| HGF | 0.002 |
| HIF fasted | 0.019 |
| HIF fed | 0.040 |

*<LOQ: below limit of quantitation.

Solubility studies of the phosphate salt were undertaken in aqueous media and in human fluids at 24 hours. Results for the phosphate salt without prior equilibration (Table 4C) and with equilibration over 24 hours in pH 1HCl (Table 4D). The latter conditions showed that the phosphate salt converted to the HCl salt over this time.

TABLE 4C

Solubility of Phosphate Salt

| Medium | Solubility in mg/ml after 24 h |
|---|---|
| SGF | 0.088 |
| FaSSIF | 0.003 |
| FeSSIF | 1.067 |
| pH 1 HCl | 0.089 |
| ph 4.5 Acetate | 0.731 |
| ph 6.8 Phosphate | <LOQ* |
| HGF | 0.0115 |
| HIF fasted | 0.00223 |
| HIF fed | 0.00141 |

*<LOQ: below limit of quantitation.

TABLE 4D

Solubility of Hydrochloride Salt Resulting from Equilibration of Phosphate Salt at pH 1, HCl

| Medium | Solubility in mg/ml after 24 h |
|---|---|
| SGF | 0.073 |
| FaSSIF | 0.003 |
| FeSSIF | 0.248 |
| pH 1 HCl | 0.075 |
| ph 4.5 Acetate | 0.822 |
| ph 6.8 Phosphate | <LOQ* |
| HGF | 0.0348 |
| HIF fasted | 0.0154 |
| HIF fed | 0.0109 |

*<LOQ: below limit of quantitation.

Example 9

FT-Raman Spectroscopy of the Free Base of the Compound of Formula I

FT-Raman spectroscopy of the monohydrate and anhydrous crystalline free base forms of the compound of Formula I was carried out as described above. The Raman spectrum for the anhydrous free base form of the compound of Formula I is shown in FIG. 8A. Peaks in FIG. 8A include 3067, 2950, 2927, 2854, 2828, 1690, 1619, 1585, 1539, 1458, 1409, 1385, 1358, 1297, 1233, 1191, 1098, 1062, 998, 819, 778, 742, 695, 668, 637, 498, 468, 420 cm$^{-1}$. The Raman spectrum for the monohydrate free base is shown in FIG. 8B. Peaks in FIG. 8B include 2957, 2831, 1618, 1580, 1511, 1465, 1415, 1361, 1312, 1284, 1229, 1186, 1148, 1057, 994, 854, 721, 661, 624 cm$^{-1}$.

Example 10

Figure 9:
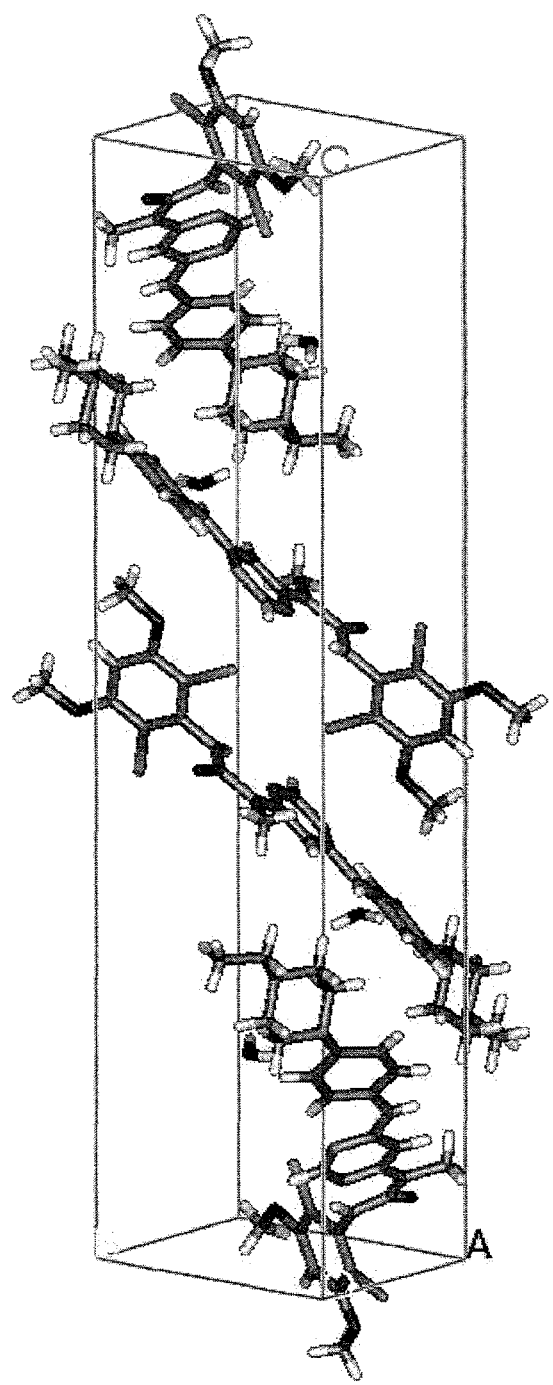
FIG. 9. Single crystal X-ray structure of the elementary cell of the free base monohydrate form of the compound of Formula I.

Single Crystal X-ray Crystallographic Analysis of the Crystalline Monohydrate Form of the Free Base of the Compound of Formula Single crystal X-ray crystallographic analysis of the crystalline monohydrate form of the free base of the compound of Formula I was carried out as described above. The results of the analysis are shown in Table 5 below and in FIG. 9.

TABLE 5

| | |
|---|---|
| Crystal size (mm) | 0.16 × 0.08 × 0.06 |
| Cell dimensions in angstroms (Å) and degrees (°) | a = 7.7615(2) Å |
| | b = 9.3168(2) Å |
| | c = 37.8111(8) Å |
| | α = 90° |
| | β = 91.439(2)° |
| | γ = 90° |
| | V = 2733.35(11) Å$^3$ |
| Space group | P21/c |
| Molecules/unit cell | 4 |
| Density | 1.362 |

Demonstration of the Stability of the Crystal Forms

Example 11

Solution Stability

The solution stability of the free base was tested in buffers ranging from pH 1 to pH 9 for 1 week at 50° C. At pH 5 and higher, the free base was stable, and after accounting for minor initial impurities, degradation was less than 2%. At pH 3, degradation was about 4% and at pH 1, degradation was about 15%. The stability was also tested in water and several organic solvents (1 week at 50° C.). The free base was stable in isopropanol and showed from about 6 to 7% degradation in acetonitrile and methanol.

The phosphate salt, form A, was stable in isopropanol and acetonitrile, and showed about 8% degradation in methanol. In water, the free base was stable, but the phosphate salt showed about 45% degradation. This does not impact the administration of the phosphate salt orally; in fact, as demonstrated below, the phosphate salt has about a 2-fold higher bioavailability than the free base. Without being bound by mechanism, the stability difference between the free base and phosphate salt may be due to the higher aqueous solubility of the phosphate salt compared to the free base, as well as the tendency of the phosphate salt to cause the pH of water to decrease, which may increase the rate of degradation. Both the free base and phosphate salt showed the highest degradation in 1:1 acetonitrile/water (about 8% and 70%, respectively).

Based on HPLC-MS analysis, it appears that the urea functionality of the free base is hydrolyzed as shown below resulting in two major hydrolysis products. The two major degradation peaks by HPLC-MS showed the expected molecular ions (MH$^+$=313 for HPLC peak at 2.1 min, and MH$^+$=222 for HPLC peak at 8.6 min). As further confirmation, an authentic sample of 2,6-dichloro-3,5-dimethoxyaniline was also injected into the HPLC and the retention time and UV spectrum showed satisfactory agreement with the later eluting HPLC degradation peak.

Example 12

Solid State Stability

In the solid state, the samples were stressed for one week at 80° C., in sealed containers and under 75% relative humidity. The crystal forms of the anhydrous free base and the phosphate salt (form A) were demonstrated to be stable in the solid state, alone, and in presence of excipients as a 1% mixture. The amount of degradation products of the anhydrous free base as assessed by HPLC was 1% or less (based on peak area), while the degradation of the phosphate salt accounted for 1.4% or less. The XRPD of each polymorph showed no change of form.

Example 13

Effect of Equilibration with Solvents

A. Room Temperature

About 20 mg of the phosphate salt (form A) was equilibrated with 2 ml of a variety of solvents for at least 24 h at room temperature. Then the solution was filtered and the residue dried overnight at 50° C. under house vacuum. The solid obtained was investigated by XRPD. No new XRPD pattern was observed for the solvents listed in Table 6. These results demonstrate the polymorphic stability of the phosphate salt (form A).

The free base was equilibrated in water, ethanol, isopropanol, ethyl acetate, and acetone, and as above, analyzed by XRPD. No new XRPD pattern was observed.

Scheme 1: Proposed Degradation Pathway in Water

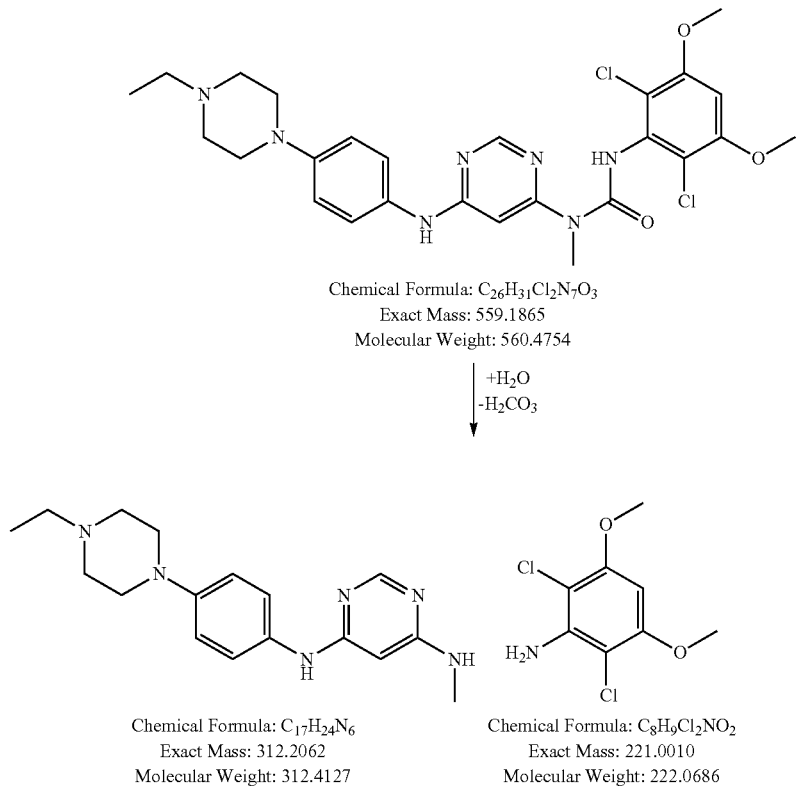

TABLE 6

Solvents Used for Equilibration Experiments at 25° C.
Solvents

Methanol
Ethanol abs.
Ethanol 95%
2-Propanol
Acetonitrile
Acetone
Tetrahydrofuran
Toluene
Methylene chloride
Dioxane
DMF
DMSO
Water
Methanol/Water 9:1
Methanol/Water 1:1
Methanol/Water 1:9
Ethanol/Water 50:50
Ethanol/Water 10:90
2-propanol/Water 90:10
2-propanol/Water 50:50
2-propanol/Water 10:90
Acetone/Water 50:50
Acetone/Water 10:90
Acetonitrile/Water 90:10
Acetonitrile/Water 50:50
Acetonitrile/Water 10:90
Tetrahydrofuran/Water 1:1
Tetrahydrofuran/Water 1:9

B. 50° C.

About 20 mg of the phosphate salt (form A) was also equilibrated at about 50° C. with 2 ml solvent for at least 24 h. Then the solution was filtered and the residue dried overnight at 50° C. under house vacuum. The solid obtained was investigated by XRPD. No new XRPD pattern was observed for any solvent listed in Table 7. These results demonstrate the polymorphic stability of the phosphate salt (form A).

TABLE 7

Solvents Used for Equilibration Experiments at 50° C.
Solvents

Methanol
Ethanol abs.
Ethanol 95%
2-Propanol
Acetonitrile
Acetone
Ethyl acetate
Propyl acetate
Tetrahydrofuran
Toluene
Dioxane
Methyl t-butyl ether
DMSO
Water
Methanol/Water 90:10
Methanol/Water 50:50
Methanol/Water 10:90
Ethanol/Water 50:50
Ethanol/Water 10:90
2-propanol/Water 90:10
2-propanol/Water 50:50
2-propanol/Water 10:90
Acetone/Water 90:10
Acetone/Water 50:50
Acetone/Water 10:90
Acetonitrile/Water 90:10
Acetonitrile/Water 50:50
Acetonitrile/Water 10:90
Tetrahydrofuran/Water 90:10

TABLE 7-continued

Solvents Used for Equilibration Experiments at 50° C.
Solvents

Tetrahydrofuran/Water 50:50
Tetrahydrofuran/Water 10:90

Example 14

Effect of Crystallization from Hot Saturated Solutions

About 20 mg of the phosphate salt (form A) was dissolved in 2 ml solvent at 60° C. The solution was filtered. The clear filtrate obtained was cooled in an ice bath and agitated. The precipitate was collected on a filter, dried and investigated by XRPD. No change in polymorphic form was observed upon crystallization from 1:1 solutions of water with methanol, ethanol, 2-propanol, acetone, and tetrahydrofuran. Only using DMSO was a form change noted by XRPD. These results demonstrate the polymorphic stability of the phosphate salt (form A).

Example 15

Effect of Crystallization by Evaporation

A. 25° C.

About 20 mg of the phosphate salt (form A) was mixed with 2 ml solvent at 25° C. After stirring overnight, the solution was filtered. The filtrate was placed under nitrogen flow to evaporate the solvent. The residual solid was collected and investigated. The above evaporation was performed without stirring. Upon evaporation from THF/water (1:1) without stirring, a solid with XRPD pattern similar to that of the B form (see FIG. 1C), was obtained once. Subsequently, under these conditions, amorphous material, rather than form B, was obtained. Similarly, amorphous material was obtained from evaporative crystallization from 1:1 solutions of water with ethanol, 2-propanol, acetone, and tetrahydrofuran. When the solution was stirred during evaporation, form A was consistently obtained; demonstrating the polymorphic stability of the crystalline form of the phosphate salt (form A).

B. 50° C.

The same experiments (as described above for the 25° C. evaporation) were performed at 50° C. Under these conditions, amorphous material was obtained from only some of the unstirred solutions. As shown in Table 8, other unstirred solutions yielded Form A. Form A was also obtained when the solution was stirred, demonstrating the polymorphic stability of the crystalline form of the phosphate salt (form A).

TABLE 8

Effect of Crystallization by Evaporation at 50° C.

| Solvent | XRPD Result |
|---|---|
| Methanol/water 1:1 | — |
| Ethanol/water 1:1 | Amorphous |
| 2-propanol/water 1:1 | — |
| Acetone/water 1:1 | — |
| Acetonitrile/water 1:1 | Amorphous |
| Tetrahydrofuran/water 1:1 | — |

"—": no change detected.

Example 16

Effect of Precipitation by Addition of Solvent

Two different solvent combinations were tested. The phosphate salt (form A) was dissolved in DMSO where its solubility was high. A solvent (the anti-solvent) in which the form A was highly insoluble was added to the solution. The precipitate was collected on a filter, dried, and investigated by XRPD. No change in Form was observed for any of the following solvents: methanol, ethanol, isopropanol, acetone, acetonitrile, THF, ethyl acetate, propyl acetate, toluene, methyl t-butyl ether, 1,4-dioxane, methylene chloride. These results demonstrated the polymorphic stability of the crystalline form of the phosphate salt (form A).

Example 17

Stability under Compression

The phosphate salt (form A, 300 mg) was compressed for 5 minutes at 4000 pounds with a hydraulic press (diameter of the tablets 8 mm). No change of crystalline modification was observed by XRPD. These results demonstrated the stability of the crystalline form of the phosphate salt (form A).

Example 18

Stability under Granulation

A solvent (water or ethanol) was added drop wise to the phosphate salt (form A) placed in a mortar until the solid in the mortar was sufficiently wet, and ground using a pestle until a paste-like consistency was obtained. The paste was dried at around 40° C. and under reduced pressure for >8 hours. The solids were evaluated by XRPD, and no changes in the XRPD spectra were observed. These results demonstrated the stability of the crystalline form of the phosphate salt (form A).

Example 19

Stability under Heating and Cooling

This was observed following the second DSC run after melt quenching. The onset of the melt was noted at 183.2° C. The sample started to decompose at 185.9° C., right after the melt onset. No further testing was conducted.

Example 20

Water Sorption and Desorption Experiments

Figure 4A:
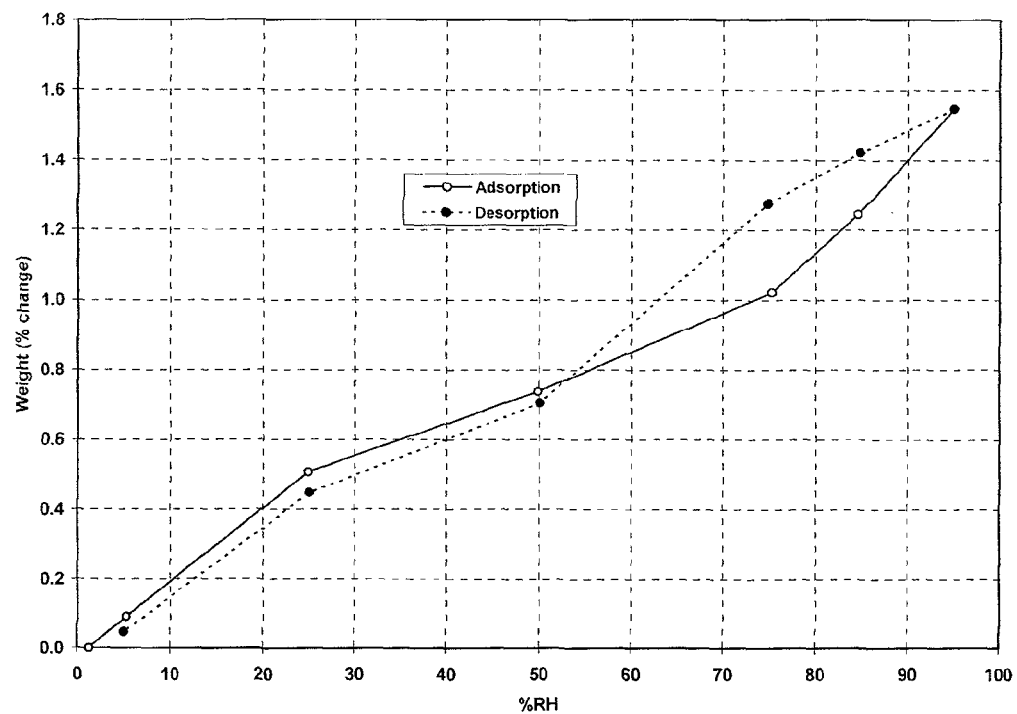
FIGS. 4A-4C. Sorption-desorption isotherms for the compound of Formula I as the anhydrous free base (FIG. 4A), as the phosphate salt (form A, FIG. 4B) and as the monohydrate free base (FIG. 4C) collected by DVS at 25° C.
Figure 4B:
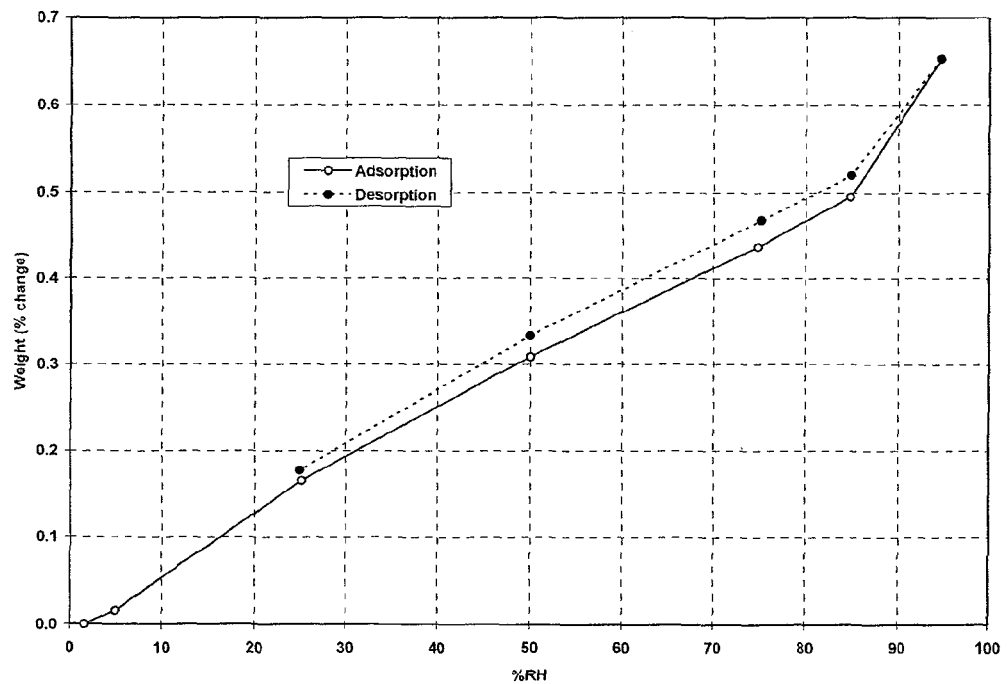
Figure 4C:
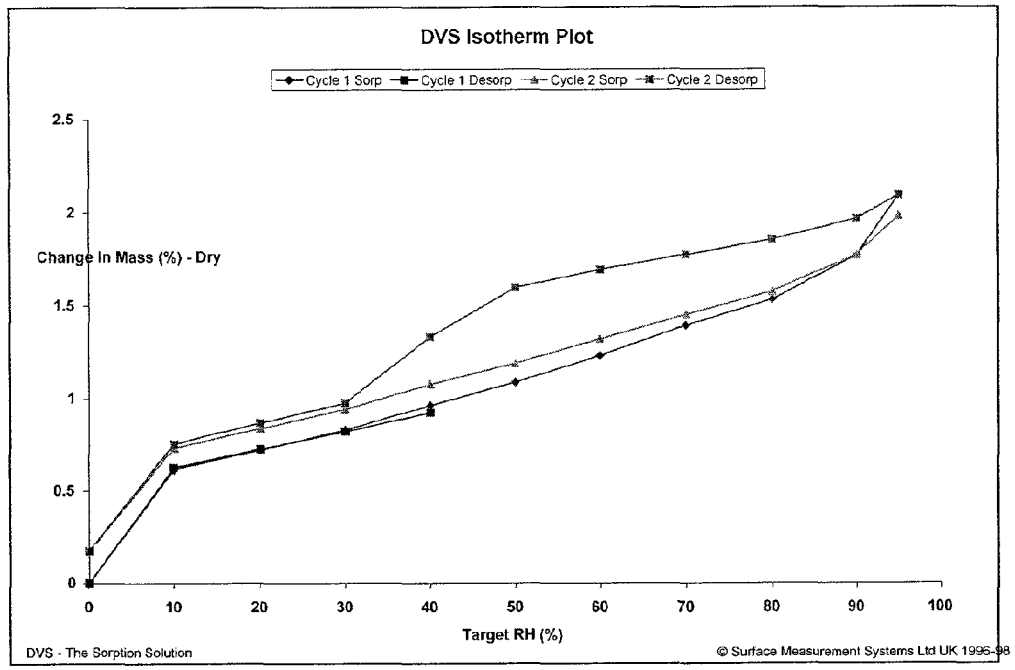

The free base (anhydrous and monohydrate) and its phosphate salt (form A) were subjected to sorption and desorption cycle using a VTI brand instrument. The solids were collected after the experiment and analyzed. FIGS. 3A (free base) and 3B (phosphate salt (form A)) shows the water sorption-desorption isotherm recorded on a TGA instrument. The DVS plots are shown in FIGS. 4A (free base, anhydrous), 4B (phosphate salt (form A) and 4C (free base, monohydrate). The maximum water uptake for the phosphate salt (form A) was less than 2% (i.e. 0.7%) at 25° C. up to 95% relative humidity (rh) (see Table 9). The maximum water uptake for the monohydrate was less than 1.4% at 25° C. up to 95% RH. The monohydrate with an approximate water content of 3% could not be completely dried during the experiment but the water that could be removed was reversibly reabsorbed. The plateau of existence of the monohydrate form is found to be within 10% and 95% RH with a slight hysteresis at the second desorption cycle.

TABLE 9

DVS Test for Phosphate Salt

| Relative humidity (%) | Desorption Weight Gain (%) | Adsorption Weight Gain (%) |
| --- | --- | --- |
| 0 | 0.000 | 0.000 |
| 5 | 0.091 | 0.016 |
| 25 | 0.507 | 0.165 |
| 50 | 0.738 | 0.309 |
| 75 | 1.022 | 0.437 |
| 85 | 1.245 | 0.495 |
| 95 | 1.547 | 0.653 |
| 85 | 1.421 | 0.520 |
| 75 | 1.275 | 0.467 |
| 50 | 0.705 | 0.334 |
| 25 | 0.447 | 0.177 |
| 5 | 0.048 | 0.000 |

Superior Therapeutic Properties of the Phosphate Salt

Example 21

Pharmacokinetic Property of the Phosphate Salt

The higher water solubility of the phosphate salt compared to the free base (and other acid salts, as described above) led to the development of a solution formulation (or composition), which would not be feasible with the free base due to solubility restrictions. For this experiment, the phosphate salt was prepared as follows. In a glass vial, 10.7 mg of the free base was dissolved in 4 ml THF. Phosphoric acid (1.76 ml) in acetone (0.01M) was added. The mixture was warmed to 50° C. for about 2 minutes. The vial was left open for partial evaporation at room temperature. Overnight, a suspension was formed, which was filtered yielding about 5.5 mg of an off-white powder. The bioavailabilities, in rats, of the active agents (the free base and its phosphate salt), formulated variously, are tabulated below (Table 10).

TABLE 10

| Pharmacokinetic parameters | Free base i.v. [5 mg/kg] | Free base p.o., colloidal solution* [10 mg/kg] | Free base p.o., suspension** [8.57 mg/kg] | Phosphate salt p.o., solution*** [10 mg/kg] | Phosphate salt p.o., suspension** [8.57 mg/kg] |
| --- | --- | --- | --- | --- | --- |
| $C_{5\,min}$ [µmol/L ± SE] | 0.972 ± 0.404 | — | — | — | — |
| $C_{max}$ [µmol/L ± SE] | — | 0.154 ± 0.026 | 0.202 ± 0.021 | 0.263 ± 0.083 | 0.150 ± 0.031 |
| $C_{last}$ [µmol/L ± SE] | 0.003 ± 0.003 | 0.010 ± 0.005 | 0.077 ± 0.038 | 0.148 ± 0.018 | 0.062 ± 0.006 |
| $t_{max}$ [h] | — | 3.0 | 2.0 | 4.0 | 3.0 |

TABLE 10-continued

| Pharmacokinetic parameters | Free base i.v. [5 mg/kg] | Free base p.o., colloidal solution* [10 mg/kg] | Free base p.o., suspension** [8.57 mg/kg] | Phosphate salt p.o., solution*** [10 mg/kg] | Phosphate salt p.o., supension** [8.57 mg/kg] |
|---|---|---|---|---|---|
| $t_{last}$ [h] | 24 | 24 | 8 | 8 | 8 |
| $t_{1/2}$ terminal elimination [h] | 4.5 | 5.2 | 4.3 | 4.8 | 4.4 |
| Cl [L/h/kg] | 3.6 | — | — | — | — |
| $V_{ss}$ [L/kg] | 9.6 | — | — | — | — |
| AUC (0-∞) [h · µmol/L] | 2.47 | 1.44 | 1.55 | 2.52 | 1.23 |
| AUC (0-∞) dose $^A$ [(h · µmol/L)/(mg/kg)] | 0.49 | 0.14 | 0.18 | 0.25 | 0.14 |
| BAV f [%] | | 29 | 37 ± 11 | 51 | 29 ± 3 |

*The free base solution is based on water, ethanol and cremophor EL.
**The suspensions were prepared in water containing 0.5% HPMC.
***The phosphate salt solution was prepared in PEG300/acetate buffer pH 4.7 (1:1 volume).

The invention claimed is:

1. A monophosphoric acid salt of the compound of Formula I:

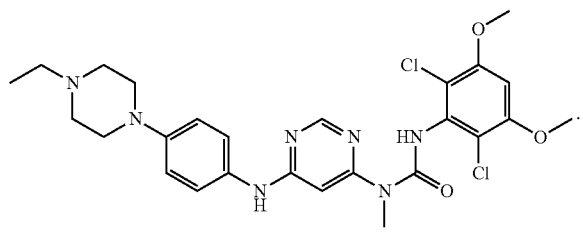

I

2. The monophosphoric acid salt of claim 1 which is the anhydrous crystalline monophosphoric acid salt.

3. The anhydrous crystalline monophosphoric acid salt of claim 2 having form A wherein the form A has an X-ray powder diffraction pattern comprising a characteristic peak, in terms of 2θ, at about 15°.

4. The anhydrous crystalline monophosphoric acid salt of form A of claim 3, wherein the X-ray powder diffraction pattern further comprises one or more characteristic peaks, in terms of 2θ, selected from peaks at about 13.7°, about 16.8°, about 21.3° and about 22.4°.

5. The anhydrous crystalline monophosphoric acid salt of form A of claim 4, wherein the X-ray powder diffraction pattern further comprises one or more characteristic peaks, in terms of 2θ, selected from peaks at about 9.2°, about 9.6°, about 18.7°, about 20.0°, about 22.9°, and about 27.2°.

6. An anhydrous crystalline form (form A) of a monophosphoric acid salt of the compound of Formula I:

wherein the anhydrous crystalline form A has an X-ray powder diffraction pattern comprising at least 3 characteristic peaks, in terms of 2θ, selected from peaks at about 13.7°, about 15°, about 16.8°, about 21.3° and about 22.4°.

7. The anhydrous crystalline form of claim 6 having an X-ray powder diffraction pattern substantially as shown in FIG. 1B.

8. The anhydrous crystalline form of claim 6 having a differential scanning calorimetry thermogram showing an onset of an endotherm at about 184° C.

9. The anhydrous crystalline form of claim 6 having a differential scanning calorimetry thermogram substantially as shown in FIG. 2B.

10. The anhydrous crystalline monophosphoric acid salt of claim 2 having form B wherein the form B has an X-ray powder diffraction pattern comprising one or more characteristic peaks, in terms of 2θ, selected from peaks at about 9.3°, about 12.5°, about 13.4°, about 15.8°, and about 17°.

11. The anhydrous crystalline form of claim 10 having an X-ray powder diffraction pattern substantially as shown in FIG. 1C.

12. The hydrochloride salt of the compound of Formula I:

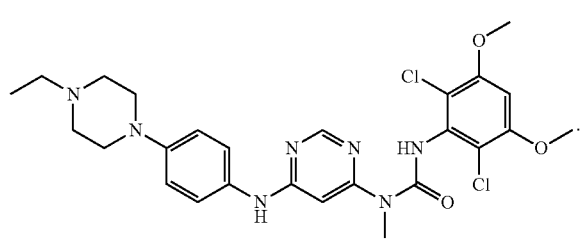

I

13. The hydrochloride salt of claim 12 which is a crystalline dihydrate.

14. The crystalline hydrochloride salt of claim 12 having an X-ray powder diffraction pattern comprising one or more characteristic peaks, in terms of 2θ, selected from peaks at about 10.9°, about 12.1°, about 14.8°, about 20.5°, about 22°, and about 25.1°.

15. The crystalline hydrochloride salt of claim 12 having an X-ray powder diffraction pattern substantially as shown in FIG. 1E.

* * * * *